United States Patent [19]

Biddle, Jr. et al.

[11] Patent Number: 4,945,490
[45] Date of Patent: Jul. 31, 1990

[54] BRINELL HARDNESS INDICATOR WITH DIGITAL READOUT

[76] Inventors: Ernest L. Biddle, Jr., 1028 Great Springs Rd., Bryn Mawr, Pa. 19010; John D. Laessig, 833 Malin Rd., Newtown Square, Pa. 19073; John B. Oehrle, 803 Newtown Rd., Villanova, Pa. 19085

[21] Appl. No.: 179,598

[22] Filed: Apr. 11, 1988

[51] Int. Cl.⁵ .......................... G06K 9/00; G01N 3/42
[52] U.S. Cl. ...................................... 364/506; 364/550; 73/81; 356/378
[58] Field of Search .................. 364/506, 550; 73/81, 73/7 R; 356/378, 379; 358/107

[56] References Cited

U.S. PATENT DOCUMENTS

| | | | |
|---|---|---|---|
| D. 283,599 | 4/1986 | Biddle, Jr. et al. | D10/46 |
| 1,209,350 | 12/1916 | Steiner | 73/81 |
| 1,770,045 | 7/1930 | Shore et al. | 73/81 |
| 1,973,333 | 9/1934 | Craemer | 265/19 |
| 2,466,567 | 4/1949 | Williams | 73/81 |
| 2,643,544 | 6/1953 | Chester | 73/81 |
| 2,693,698 | 11/1954 | Scott | 73/83 |
| 2,835,127 | 5/1958 | Scott | 73/81 |
| 2,976,723 | 3/1961 | Eddy | 73/94 |
| 3,058,001 | 10/1962 | Dertouzos | 250/208 |
| 3,128,621 | 4/1964 | Scott | 73/81 |
| 3,129,582 | 4/1964 | Borgersen | 73/81 |
| 3,138,951 | 6/1964 | Scott | 73/81 |
| 3,486,373 | 12/1969 | Scott | 73/141 |
| 3,728,551 | 4/1973 | Culver et al. | 250/231 SE |
| 3,754,436 | 8/1973 | Saxton | 73/81 |
| 3,815,125 | 6/1974 | May et al. | 340/347 P |
| 4,036,048 | 6/1977 | Webster | 73/81 |
| 4,075,478 | 2/1978 | Walker | 250/231 SE |
| 4,079,251 | 3/1978 | Osann, Jr. | 250/231 SE |
| 4,094,188 | 6/1978 | Bellouin et al. | 73/81 |
| 4,147,052 | 4/1979 | Tsujiuchi et al. | 73/81 |
| 4,193,199 | 3/1980 | Whiteley et al. | 33/1 PT |
| 4,312,220 | 1/1982 | Borgersen et al. | 73/81 |
| 4,331,026 | 5/1982 | Howard et al. | 73/81 |
| 4,361,034 | 11/1982 | Borgersen et al. | 73/81 |
| 4,372,152 | 2/1983 | Lewis et al. | 73/81 |
| 4,463,600 | 8/1984 | Hobbs et al. | 73/81 |
| 4,627,096 | 12/1986 | Grattoni et al. | 73/81 |
| 4,653,106 | 3/1987 | Yamatsuta et al. | 73/81 |

FOREIGN PATENT DOCUMENTS

| | | |
|---|---|---|
| 2357755 | 11/1973 | Fed. Rep. of Germany . |
| 2751095 | 11/1977 | Fed. Rep. of Germany . |
| 5194884 | 8/1976 | Japan . |
| 52-155588 | 12/1977 | Japan . |
| 0028101 | 10/1980 | United Kingdom . |

*Primary Examiner*—Parshotam S. Lall
*Assistant Examiner*—Brian M. Mattson

[57] ABSTRACT

Methods and apparatus for performing Brinell hardness test measurements produce hardness numbers and average Brinell indentation diameter readings automatically and minimize operator intervention and hence, operator error. The apparatus uses a light source, a video camera, a video image digitizer and a computer having a display device. In the method of the invention, electromagnetic radiation is applied to the indentation at an acute angle to the surface of the test specimen in which the indentation has been made. The electromagnetic radiation reflected from the indentation and the surrounding area is sensed. Differences in intensity, such as between light and dark, are digitized and the resulting digital field is numerically analyzed to produce a diameter, preferably major and minor diameters, of the Brinell hardness impression. The diameter or major and minor diameters are used to compute a Brinell hardness number which is displayed by the computer.

22 Claims, 20 Drawing Sheets

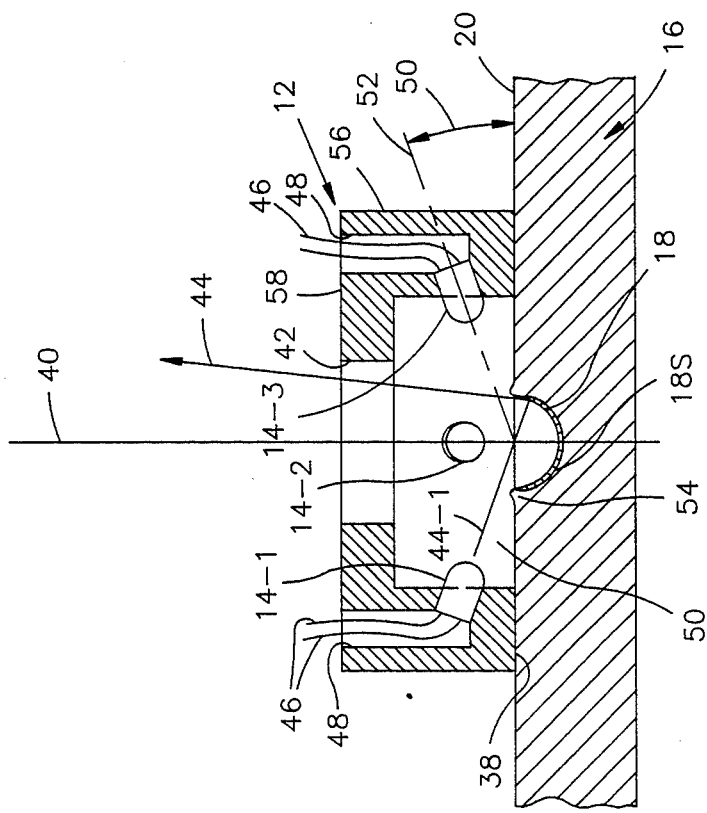

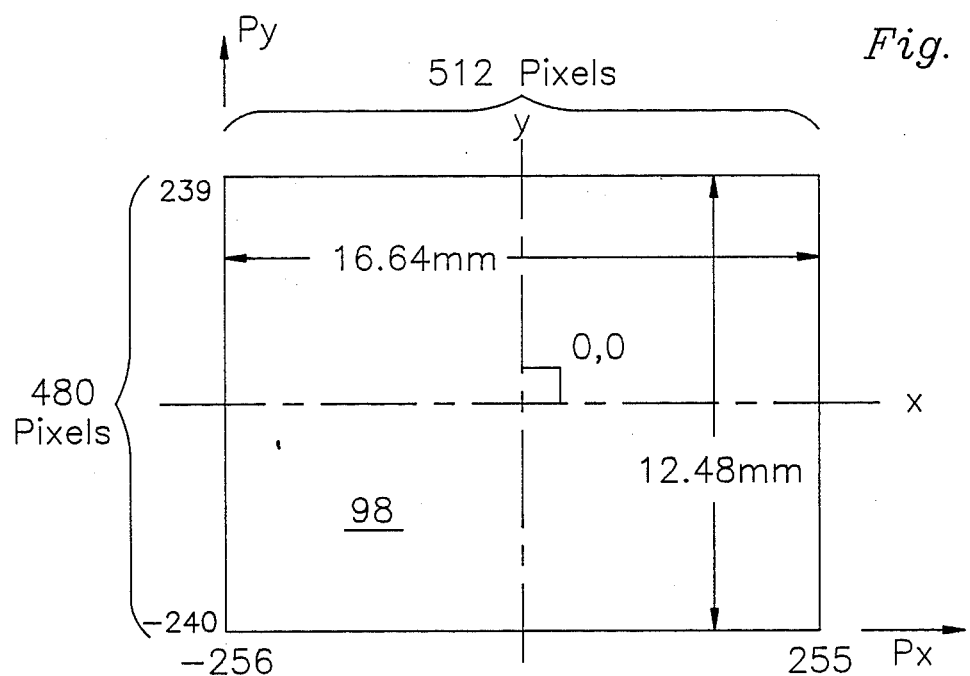
Fig. 8-A
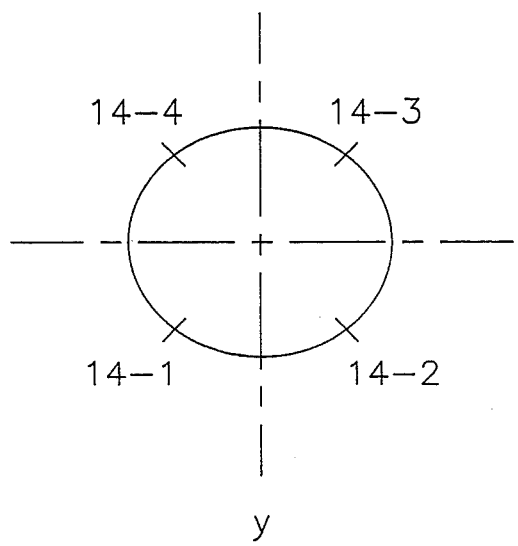
Fig. 8-B
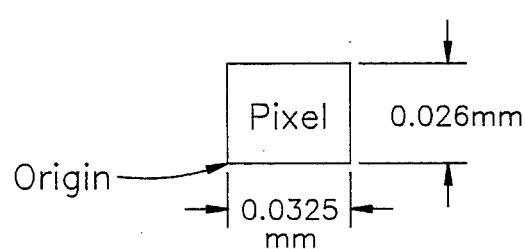
Fig. 8-C

BRINELL HARDNESS INDICATOR WITH DIGITAL READOUT

BACKGROUND OF THE INVENTION

1. Field of the Invention

This invention relates generally to metal hardness testing and specifically to digital readout of Brinell specimen indentation diameter metal hardness test results when a Brinell penetrator has been applied to a test specimen using preselected force according to Brinell specimen indentation diameter test criteria.

2. Description of the Prior Art

Specimen indentation diameter testing, most commonly referred to as Brinell hardness testing, has long been known as one of the two principal means of testing the hardness of metals, the other well-known means being the specimen indentation depth test. In such Brinell hardness testing, a penetrator is applied to a test specimen, where the penetrator is a generally blunt probe, applied according to a predetermined load. The probe produces an indentation in the test specimen, with the diameter of the indentation, when related to the force with which the penetrator is applied, defining Brinell hardness of the test specimen. Typically, diameter of the indentation is measured along two axes, perpendicularly disposed respecting one another. (This is because many times the indentation actually is an ellipse, as opposed to a circle.) The two diameters, referred to as major and minor diameters, are averaged to produce a diameter of a circle, which is used to compute Brinell hardness of the test specimen.

Such Brinell hardness testing is favored over penetration testing because such Brinell tests are generally recognized as more accurate than penetration tests. This is because Brinell tests involve a greater area of the test specimen and apply a higher load to the area. Because more area is involved, greater accuracy of the test reading is inherent.

Heretofore, indentation depth testing has been the only high-speed, high production type of testing. This is because heretofore, there has not been means or methods for accurately and quickly measuring the diameter of the impression produced utilizing the Brinell technique. Because penetration depth can be relatively easily and relatively quickly measured, indentation depth testing has been the only high speed, high production metal hardness testing heretofore.

To solve the long-standing problem of accurately and automatically measuring diameter of a Brinell hardness indentation, artisans have utilized small video cameras to obtain a picture of the indentation and computers to digitally resolve the indentation picture, to derive the indentation diameter, which is the classic representation of Brinell hardness.

To date, results have been disappointing, principally because of poor edge definition of the detected indentation. Light sources used heretofore have not adequately illuminated the edge and have not provided adequate definition of the edge structure relative to surrounding area. Known equipment employs a video camera directly over the indentation, having a lens system looking straight down into the indentation. Typically, a light source is placed next to the camera to produce an angle of incidence of the applied light beam, relative to the indentation and the surrounding area, which is nearly perpendicular to the indentation bottom and nearly perpendicular to the plane of the test specimen surface surrounding the indentation.

In such systems, the light emitted by the light source strikes the indented area and the area surrounding the indentation; the light is reflected from both the indentation and the surrounding area with approximately the same intensity and the same amount of scattering. If the surface of the test specimen surrounding the indentation has structure similar to the portion of the test specimen which has been indented (which is frequently the case in industrial applications, where the test specimen may be unpolished or have a rough surface in the test area) light reflections back to the camera from the indentation and the surrounding area produce a low resolution image of the indentation edge, or perhaps no image of the edge at all.

Patent prior art known to applicants consists of U.S. Pat. Nos. 1,209,350, 1,232,782, 1,384,389, 1,646,195, 1,770,045, 1,973,333, 2,319,208, 2,418,916, 2,448,486, 2,466, 567, 2 535,830, 2,643,544, 2.693,698, 2,804,769. 2,835,127, 2,976,723, 3,102,417, 3,128,621, 3,138,951. 3.295,363, 3,478,568, 3,486,373, 3,728,551, 3,754,436, 3,815,125, 3,822,946, 4,036,048, 4,075,478, 4,094,188, 4,147,052, 4,193,199, 4,312,220, 4,372,152 D 178,060, D 228,174, and D 283,599; Japanese patent publications Nos. 51-94,884 and 52-155,588; German patent publications Nos. 2,357,755 and 2,751,095; and Russian Pat. No. 358,648. Of these, U.S. Pat. Nos. 3,822,946 and 4,372,152 are believed to be the most relevant.

Non-patent printed prior art known to applicants includes the publication *Introdyne Universal Horizontal Hardness Tester,* published by Blue River Laboratories, RD #4, Box 76, Lewistown, Pa. 17044; *Hirth Mini Meter for Accurate Measuring* published by Falkimer Machinery Company, Ltd., Famacoy House, Goulburn Street, Sydney, Australia and a brochure entitled *Foundrax Brinscan* supplied by Foundrax Corporation in Great Britain.

SUMMARY OF THE INVENTION

In one of its aspects, this invention provides apparatus for determining Brinell hardness of a metal test specimen having been indented by a Brinell penetrator applied with a preselected force according to Brinell test criteria and includes electromagnetic radiation source means for applying electromagnetic radiation to the indentation and to the area of a test specimen surrounding the indentation. The electromagnetic radiation is preferably applied at an acute angle relative to an axis which is generally perpendicular to the indentation, where the axis is essentially perpendicular to the area of the test specimen surrounding the indentation and is preferably the line along which the test penetrator was applied to the test specimen to produce the indentation.

One principal advantage of the invention is that it is not necessary to precisely position the indentation and the area of the test piece there surrounding at a prescribed, predetermined location relative to the electromagnetic radiation source means; the indentation and the area of the test piece there surrounding may be positioned at a range of positions.

The invention further includes means for detecting the edge of the indentation by sensing electromagnetic radiation reflected by the indentation and by the portion of the test specimen bounding the indentation. Further included are means for computing diameter of the indentation and means for converting the computed diameter to a Brinell hardness for a given test specimen. The invention may further include means for displaying a digital representation of the computed Brinell hardness based on computed indentation diameter.

The means for detecting the edge of the indentation by sensing electromagnetic radiation reflected by the indentation and by the portion of the test specimen surface surrounding the indentation preferably further comprises means for providing a signal indicative of the sensed radiation over the workpiece indentation and area theresurrounding. The sensing means is preferably a charge-coupled device camera, connected to means for digitizing the output from the camera to produce an output signal matrix consisting of a field of digitized signals corresponding to radiation intensity sensed by the charge-coupled device camera.

In yet another of its aspects, the invention provides a method for determining Brinell hardness of a metal test specimen, which includes indenting the specimen, positioning the specimen indentation generally within the field of illumination of an electromagnetic radiation source and illuminating the specimen indentation and surrounding area at an acute angle to the surface area surrounding the specimen indentation. The illuminating may be performed one time, two times, from opposite sides of the specimen indentation, or may be performed four or some other number of times, at separate positions preferably evenly circumferentially spaced around the indentation. The positions of illumination each preferably but not necessarily have a separate source of electromagnetic radiation associated therewith. The angle at which the illumination is applied to the test specimen is not particularly critical, so long as the illumination produces a shadow in the indentation. For extremely hard test specimens, where the Brinell hardness impression is relatively shallow, low angles of incidence (where the angle of incidence is the angle between the applied radiation and the surface of the test specimen surrounding the indentation) may be necessary in order to obtain the requisite shadow.

The method further includes detecting juncture of the indentation with the surrounding metal, computing diameter(s), preferably both major and minor, of the indentation by considering the indentation to be elliptical, converting the computed diameters into a Brinell hardness and displaying a digital representation of the Brinell hardness.

This invention solves the problem of low indentation resolution or low level of light reflection from shallow indentations in test specimens, by employing a light source or sources to illuminate the indentation and surrounding area at a low angle of incidence relative to the area surrounding the indentation. This approach illuminates the edge of the indentation and provides a shadow within at least a portion of the indentation, thereby producing indentation edge contrast between light and dark, providing high definition for a camera or other optical sensing device.

High edge definition is achieved at the portion of the indentation rim nearest the light source when the outside surface of the test piece surrounding the indentation is illuminated and the area within the indentation, closest to the light source, is shadowed. When multiple light sources are used, the rim or edge of the indentation provides a high definition contrasting arc between the indented and surrounding areas, with the arc approaching 180 degrees. When only a single light source is used, a high definition arc of nearly 180 degrees, but just less than 180 degrees, may be used to generate the remaining portion of the circle via conventional curve fitting techniques, defining the rim of the Brinell indentation. In such case, the generated circle is considered to be an ellipse having equal major and minor diameters.

In a preferred embodiment of the invention, a plurality of light sources may be positioned around the indentation to compute a circle defining the rim of the indentation. Preferably, each light source or set of light sources is energized separately and sequentially with the computer selecting a high definition portion of the arc defining the indentation edge near a selected light source. A computer then assembles the arc segments and derives a complete circle or ellipse defining the rim of the Brinell indentation.

Brinell hardness tests performed according to this invention are two and one half to seven times more accurate than depth of penetration hardness tests.

DESCRIPTION OF THE PREFERRED EMBODIMENTS

Figure 1:
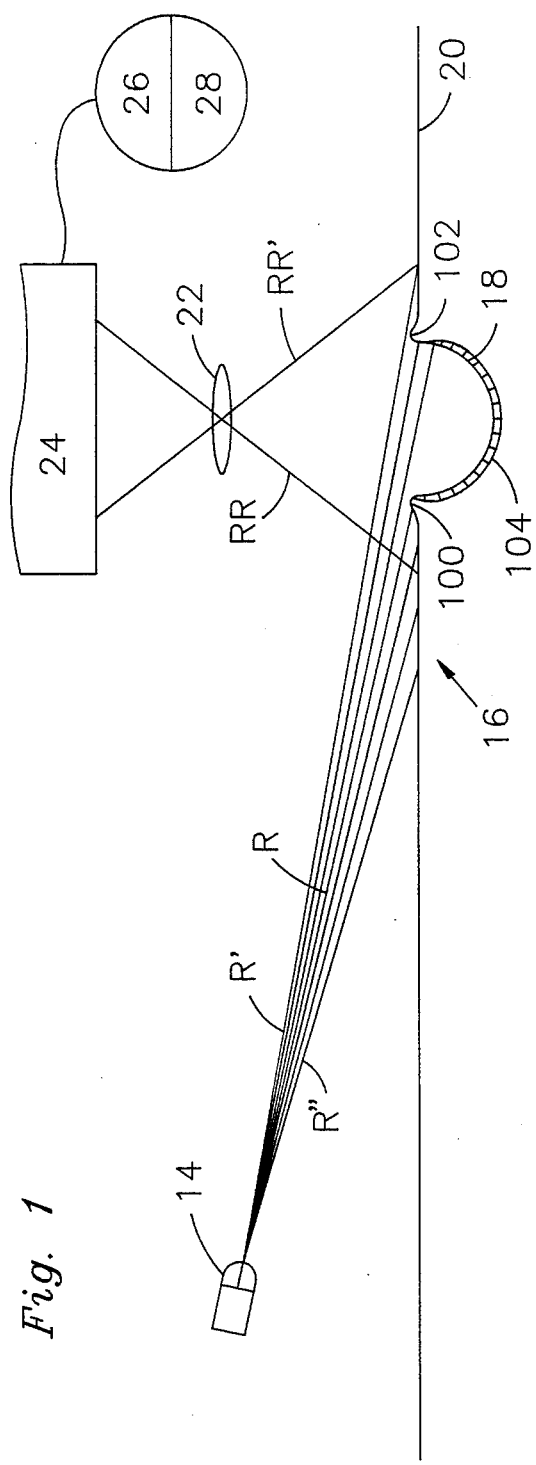
FIG. 1 is a schematic view, in side elevation, showing a Brinell indentation being illuminated by a light source and a camera or sensing device sensing radiation reflected by the indentation and the surrounding area, according to the inventors.

Referring to FIG. 1, a Brinell test specimen is indicated generally as 16, having a Brinell impression 18 formed therein and being illuminated by a light 14 with a camera 24 sensing radiation reflected by surface 20 of test specimen 16 and Brinell impression 18. Camera 24 is connected to a video digitizer and computer combination designated 26, 28 in FIG. 1. Lens 22 is provided to appropriately focus radiation reflected by surface 20 and indentation 18 for sensing by camera 24.

Figure 2:
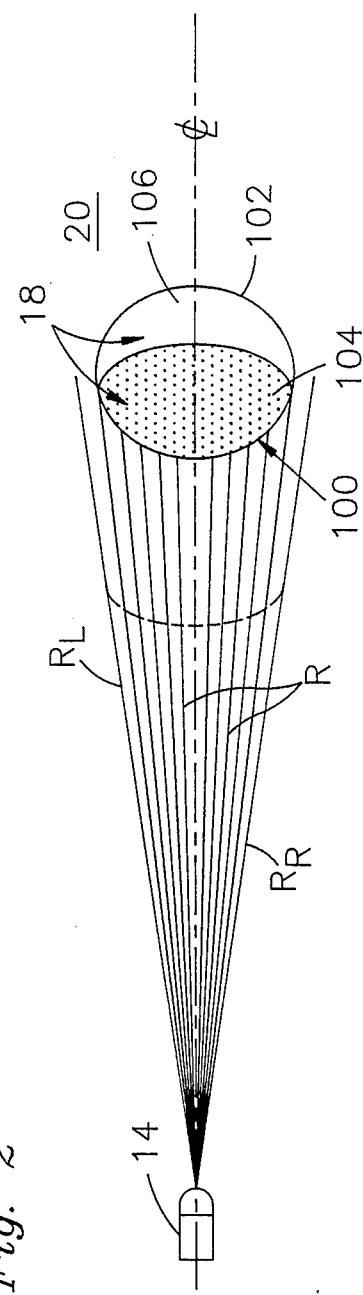
FIG. 2 is a schematic view looking downwardly from the camera illustrated in FIG. 1.

In FIGS. 1 and 2, lines R denote light rays emitted by radiation source 14. As indicated by rays RR', light source 14 emits radiation with sufficient angular spread to encompass all of indentation 18 as illustrated by ray R' intersecting surface 20, to the right of indentation 18 in FIG. 1, and ray R" intersecting surface 20 to the left of indentation 18 in FIG. 1. Radiation reflected by indentation 18 and the surrounding portion of surface 20 is sensed by camera 24, having sufficiently large field of view, when operating in conjunction with lens 22, that radiation reflected by the area of surface 20 completely surrounding indentation 18 is sensed by camera 24 as indicated by reflected rays RR' and RR in FIG. 1.

In FIG. 1, the edge portion of indentation 18 closer to FIG. 1 is denoted 100 while the portion of the edge of indentation 18 most remote from light 14 is denoted 102. As indicated by the intersection of light rays R with indentation 18, the surface of indentation 18 closest to edge 100 is shadowed while the portion of the surface of indentation 18 closest to edge 102 is illuminated by light rays R from light source 14. The shadow is indicated by the shaded arc forming a portion of the surface of indentation 18 where the shaded arc is denoted 104. Shading 104 in FIG. 2 denotes the shadowed portion of the surface of indentation 18 while 106 in FIG. 2 denotes the illuminated portion of the surface of indentation 18 which is bounded by edge 102. Shadowed portion 104 of indentation 18 is bounded by edge 100. Light source 14 has sufficient angular spread that rays $R_L$ and $R_R$ intersect surface 20 outside the lateral extremities of indentation 18.

Figure 3:
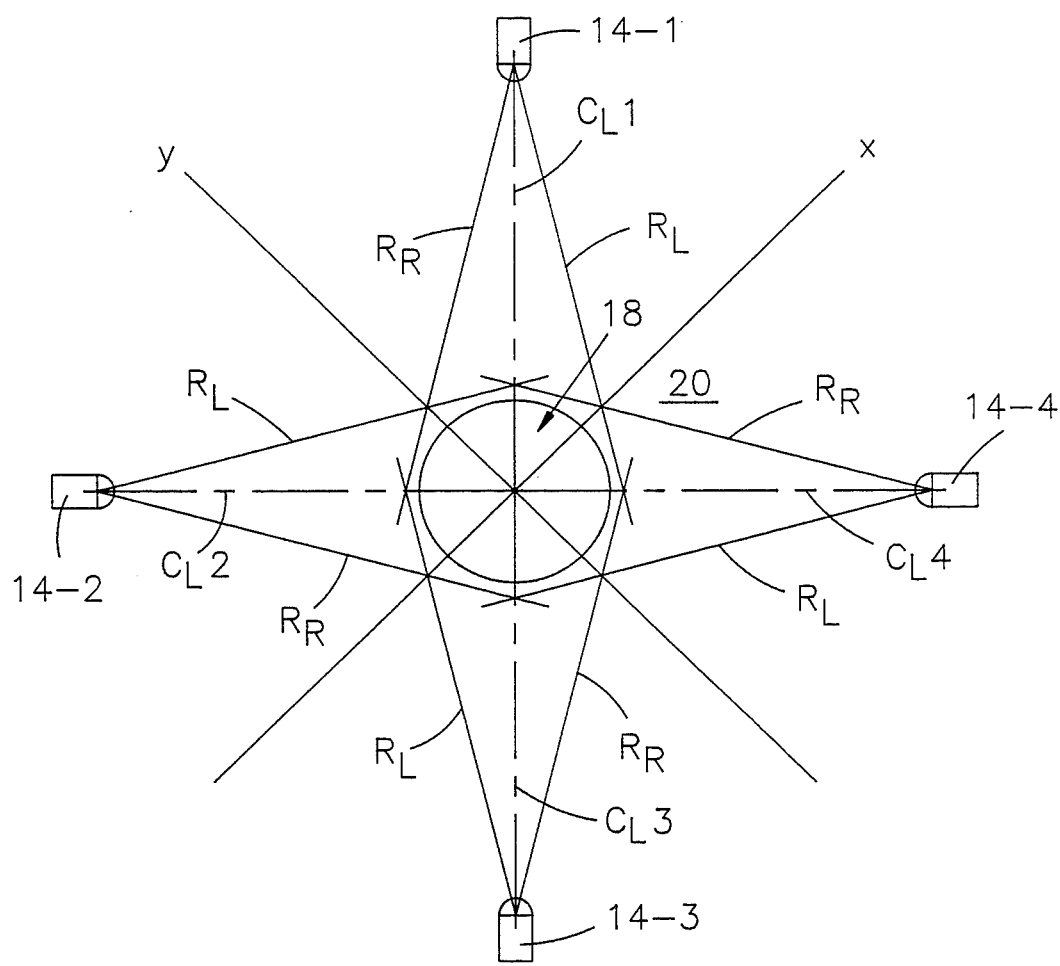
FIG. 3 is a schematic view of a Brinell indentation and four light sources radially disposed and equiangularly spaced about the Brinell indentation, as viewed by the camera illustrated in FIG. 5.

In FIG. 3, light sources 14 are indicated schematically as 14-1 through 14-4. The center lines of light sources 14-1 through 14-4 are indicated as $CL_1$ through $CL_4$ respectively and the light rays which are the extreme left and right light rays emitted by light sources 14-1 through 14-4 are indicated as $R_L$ and $R_R$ and intersect surface 20 outboard of the respective lateral extremities of indentation 18 as illustrated in FIG. 3. Also indicated in FIG. 3 are axes x and y which correspond to the axes of the field of view of video camera 24. Axes x and y are parallel with corresponding x and y axes of the camera pixel array. Axes x and y are defined by the video camera 24.

Figure 4:
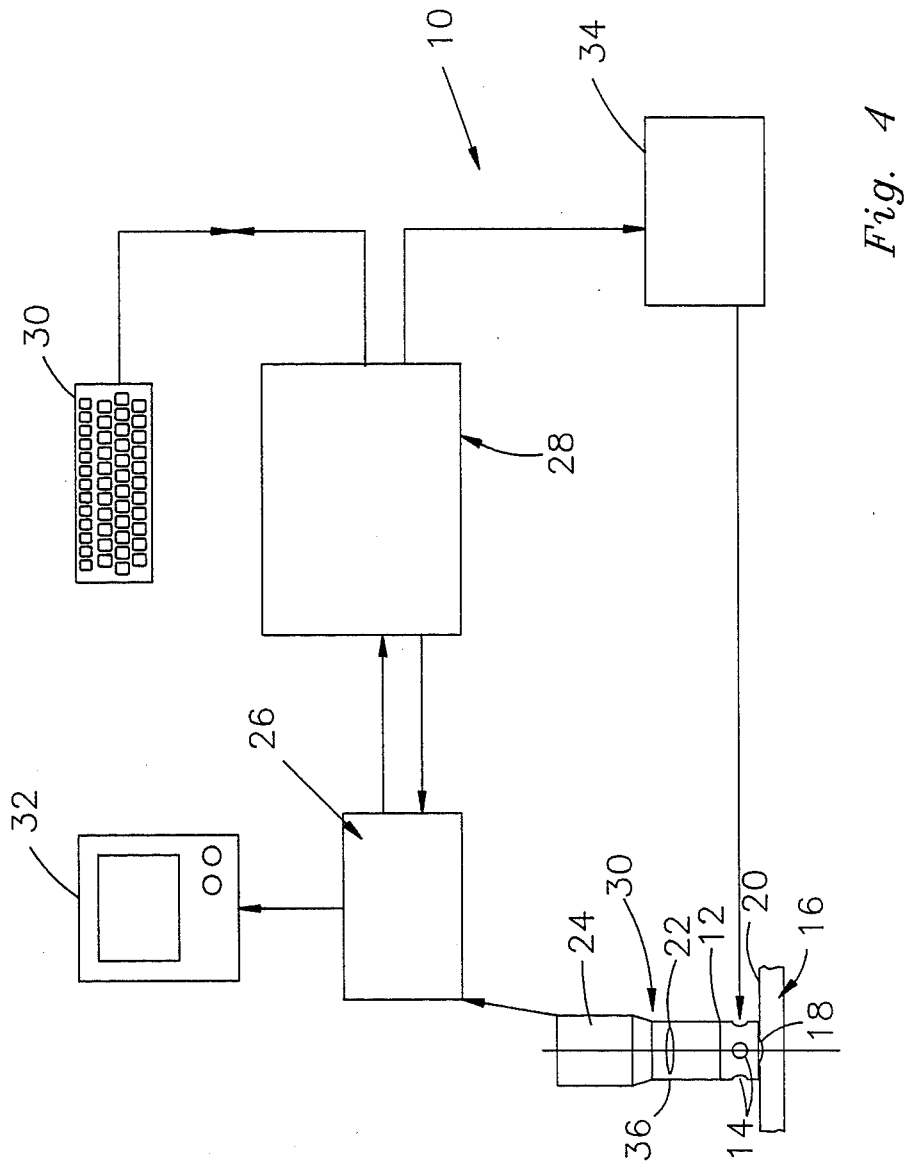
FIG. 4 is a schematic representation of apparatus embodying aspects of the invention.

Referring generally to the drawings and specifically to FIG. 4, apparatus embodying the invention is designated generally 10 and includes a light housing fixture 12, housing therewithin lights 14 and adapted to fit over a sample designated generally 16 having a Brinell indentation 18 formed in a surface 20 of the sample. A lens 22 is positioned generally above light fixture 12, at a position between test specimen 16, illuminated using lights 14, and a video camera 24, all as illustrated in FIG. 4. Video camera 24, lens 22 and light fixture 12 may all be secured together by connecting structure 36 as shown generally schematically in FIG. 4. Connecting structure 36 maintains lens 22 at a desired distance from surface 20 so that when lights 14 are illuminated, light reflected by Brinell indentation 18 and the area of the test specimen theresurrounding passes through lens 22 and is sensed by video camera 24.

Video camera 24 is connected to a video digitizer designated generally 26 which in turn is connected to a computer designated generally 28 having a keyboard 30. Also connected to digitizer 26 is a video monitor 32.

Figure 7:
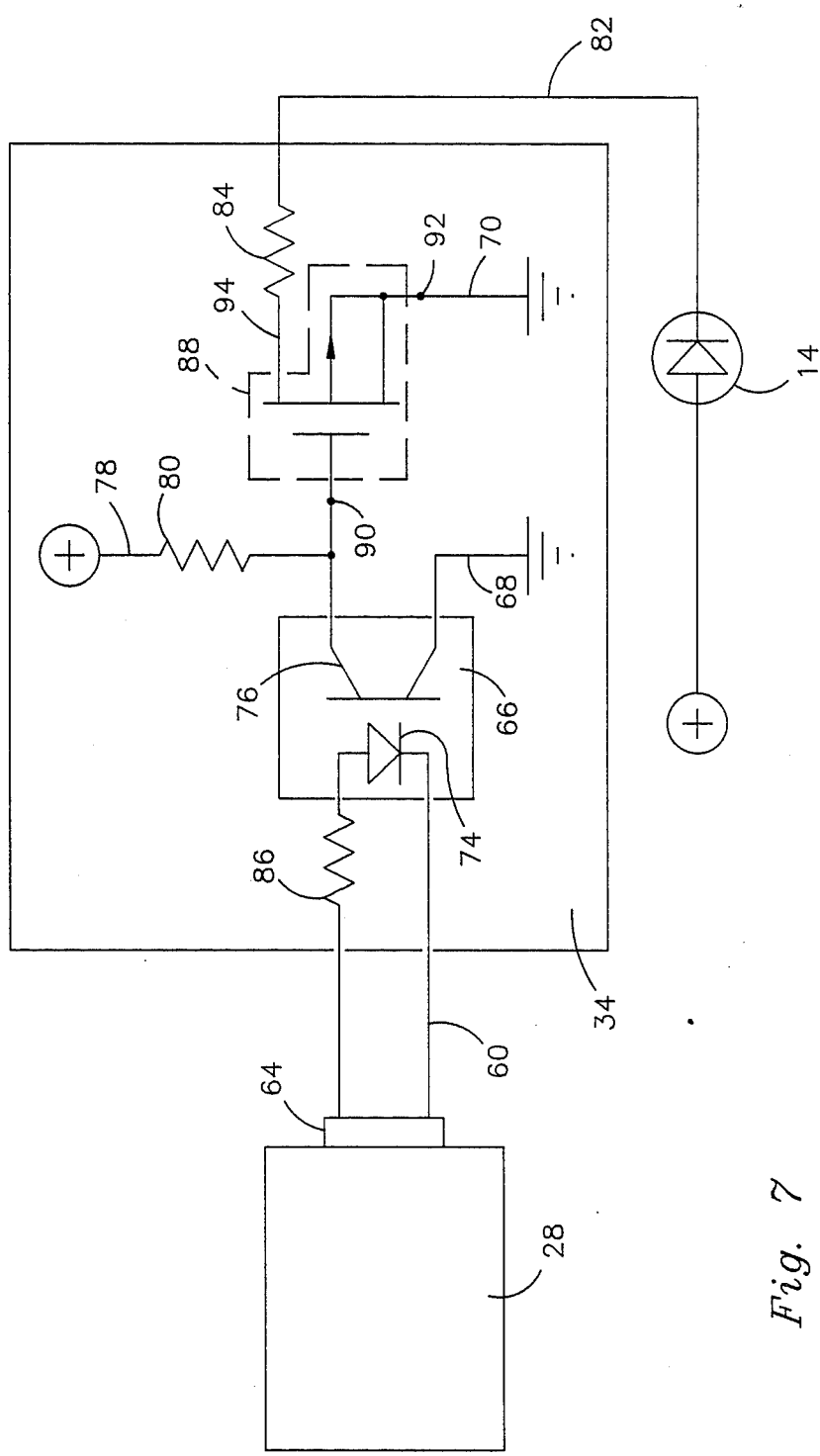
FIG. 7 is an electrical schematic of apparatus embodying aspects of the invention.

A light driver 34 receives input from computer 28 and provides output to lights 14 as illustrated schematically in FIGS. 4 and 7.

Video digitizer 26 digitizes the video representations of the Brinell indentation and surrounding area received and sensed as reflected radiation by video camera 24 and provides those digital signals in a memory buffer device controlled and accessible by computer 28. Video monitor 32 connected to digitizer 26 displays the image of the specimen Brinell indentation before a reading is taken and also displays the test results upon completion of the process for measuring Brinell hardness of the specimen.

Figures 1, 9:
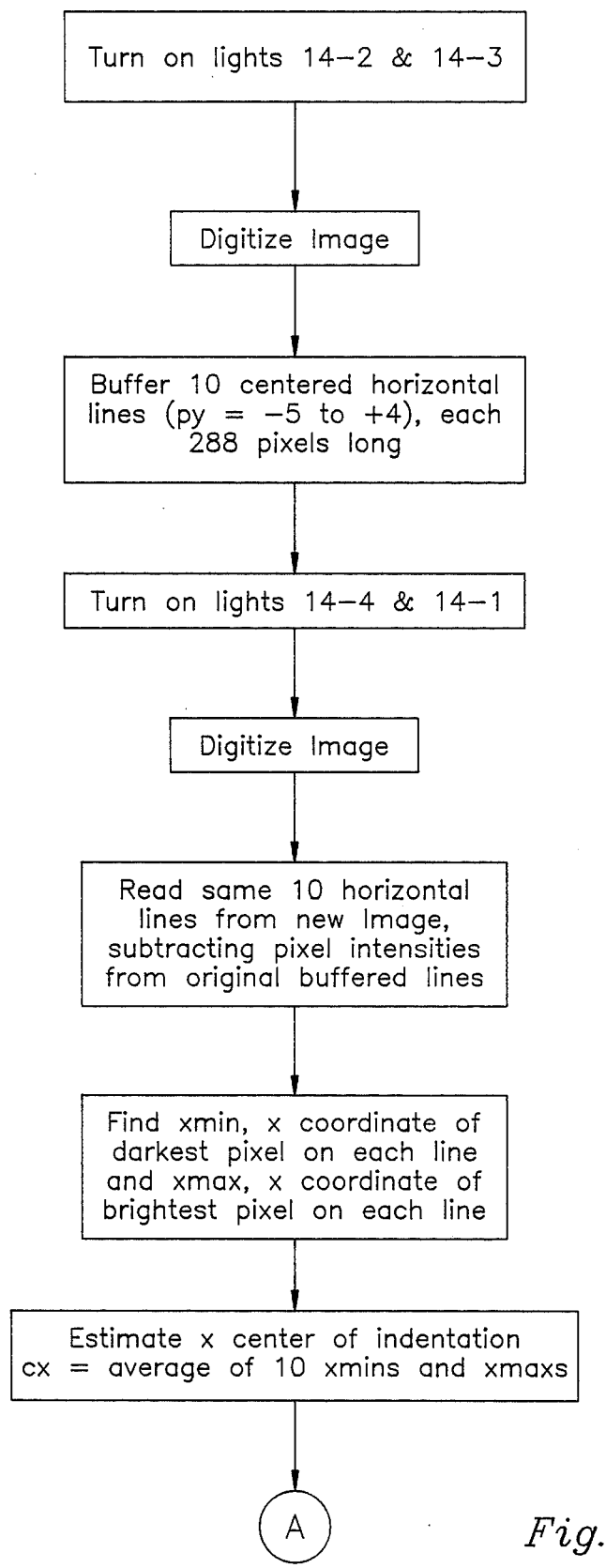
FIG. 9, consisting of FIGS. 9-1 through 9-12, is a flow chart schematically illustrating aspects of the method of the invention.
Figures 2, 9:
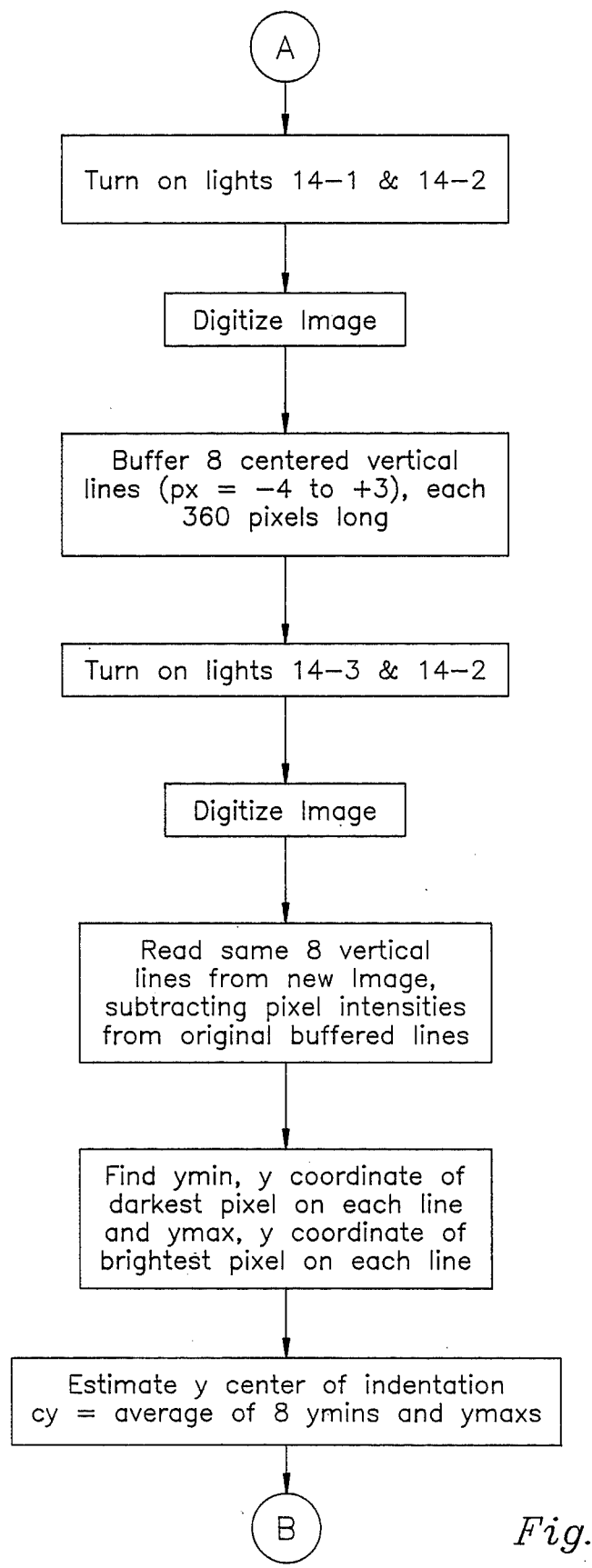
Figures 3, 9:
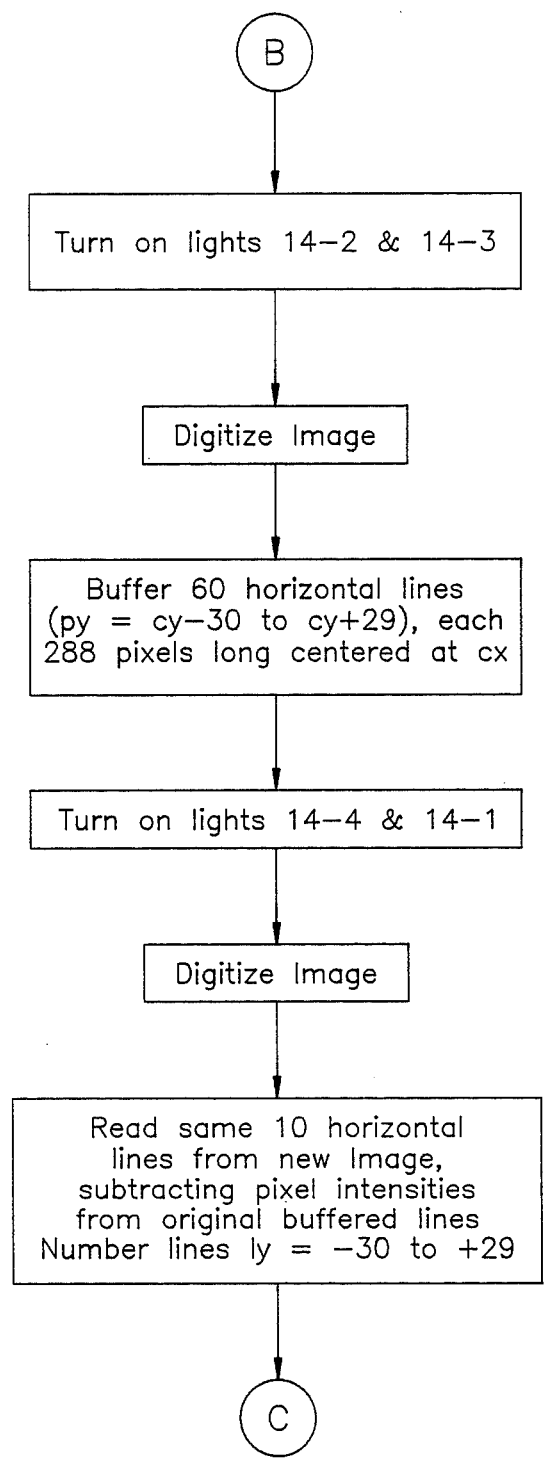
Figures 4, 9:
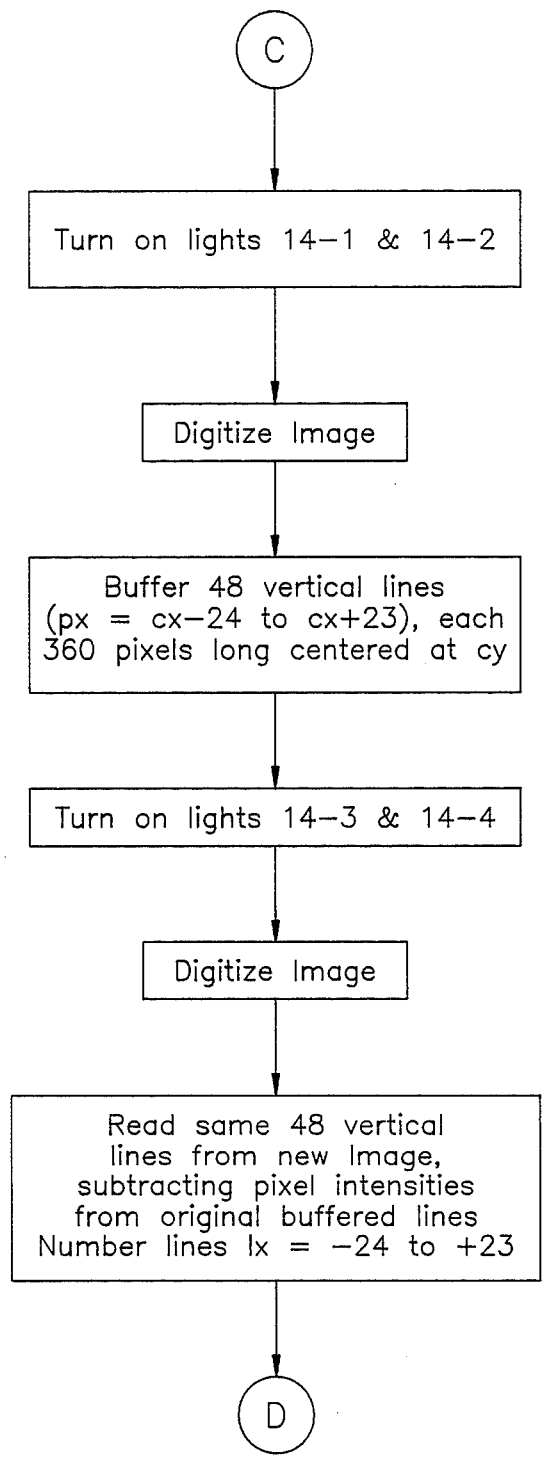
Figures 5, 9:
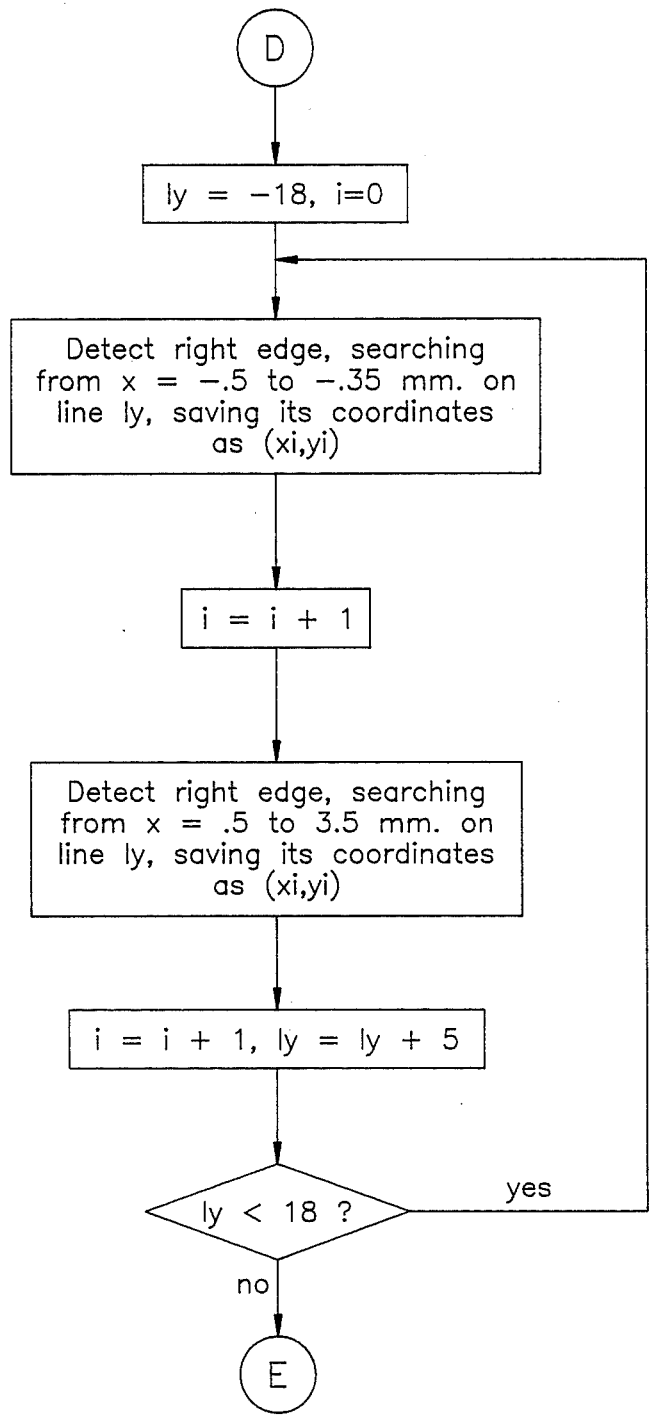
FIG. 5 is a sectional view of a portion of the apparatus illustrated in FIG. 4.
Figures 6, 9:
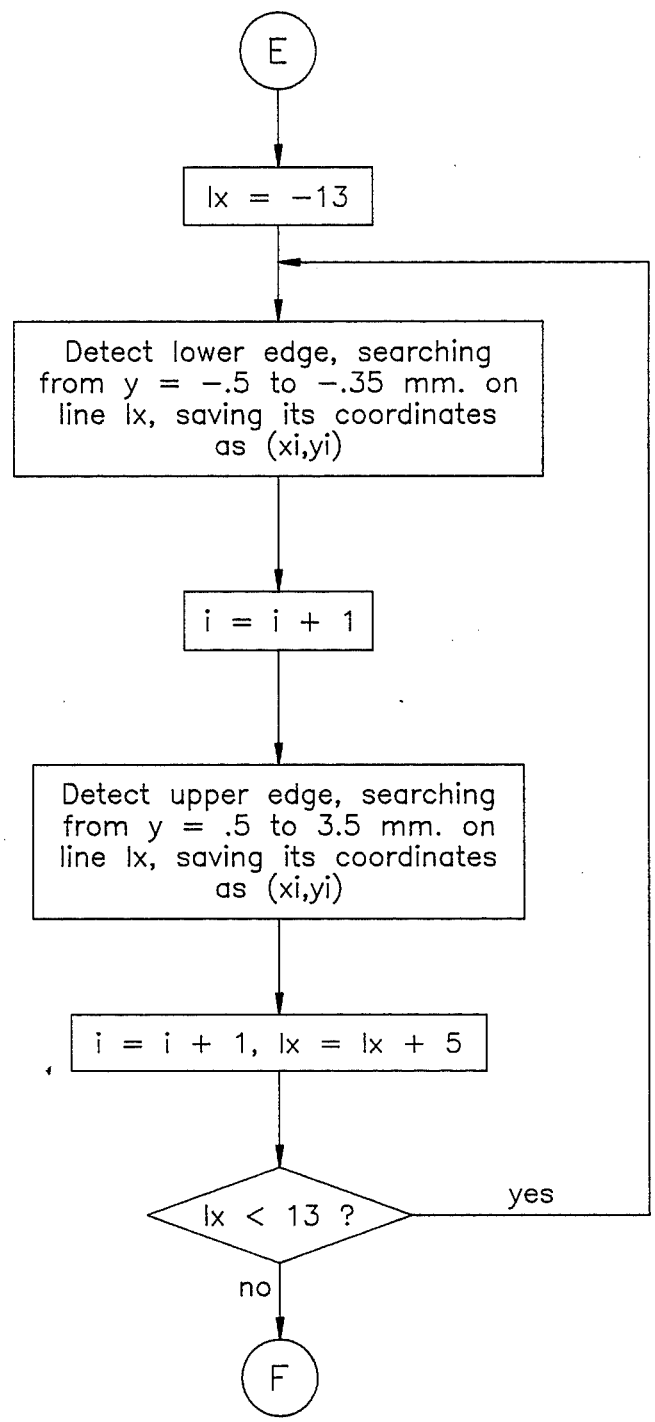
Figures 7, 9:
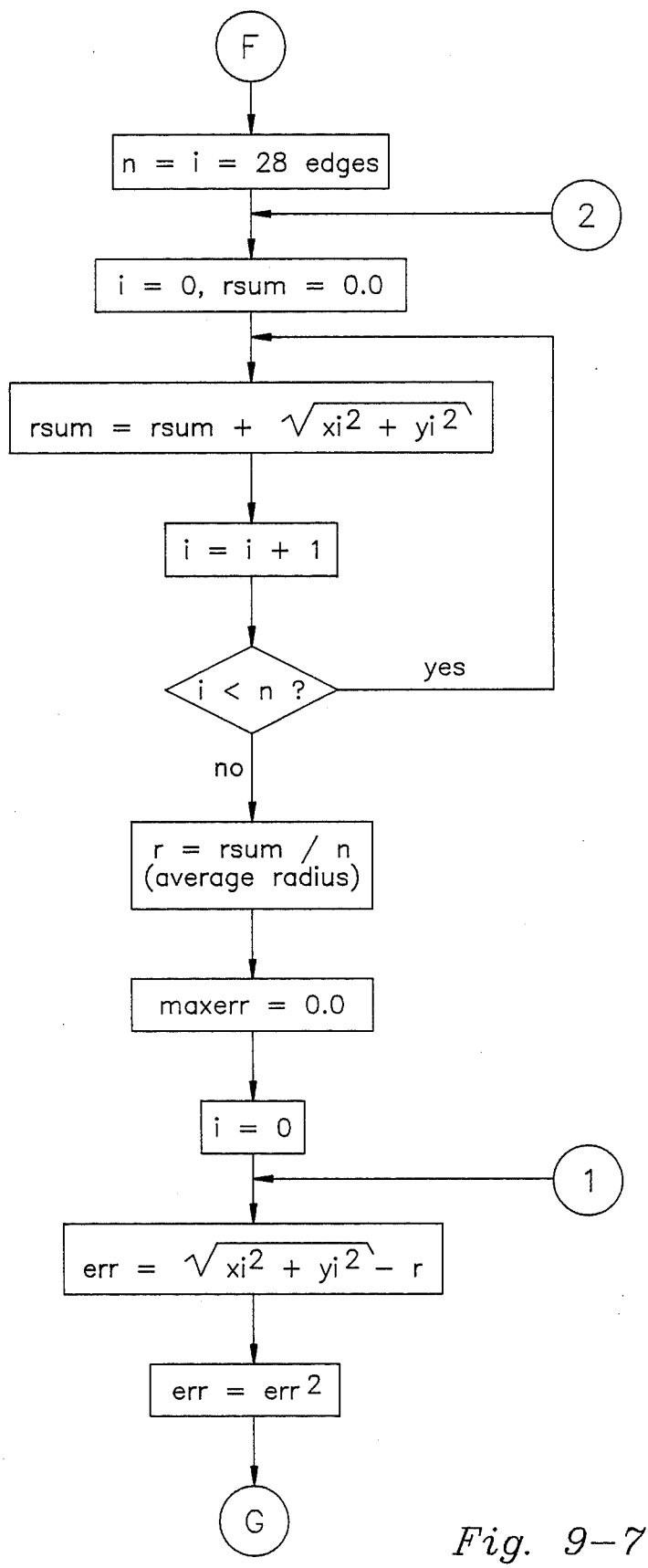

Referring to FIG. 5, the light housing fixture 12 is shown in section with lights 14 depicted therewithin with light housing fixture 12 positioned so that it is facingly abutting surface 20 of test specimen 16 in which Brinell impression 18 has been formed. Specimen 16 is movable with respect to light housing fixture 12 so that once a Brinell hardness reading is taken from one test specimen 16, that test specimen can be replaced with another test specimen or the apparatus 10 can be moved, if the light housing fixture is constructed as a portable, hand-held device, to a position to take another Brinell hardness reading for another Brinell impression in the same or a different test specimen. Hence, light housing fixture 12 facingly contacts a test specimen whose Brinell hardness is to be measured; however, light housing fixture 12 is not immovably fixed to the test specimen 16.

Light housing fixture 20 has a generally planar lower surface 38 configured for flush, facing contact with surface 20. Light housing fixture 12 is preferably of circular cross-sectional configuration in a direction generally transverse to a center line indicated as 40 in FIG. 5.

Light housing fixture 12 includes a central aperture 42 permitting light or other electromagnetic radiation reflected by Brinell impression 18 and the portion of surface 20 theresurrounding to travel generally upwardly, as shown in FIG. 5 by arrow 44, to lens 22 and hence to video camera 24, neither of which are illustrated in FIG. 5. The radiation is emitted by lights 14 and is reflected as indicated by arrow 44. While elements 14 have generally been referred to as being "lights", these elements can be any radiation emitting device, and it is not necessary that the radiation emitting devices 14 be lights emitting light in the visible spectrum. Indeed, infrared radiation may be preferable in practicing the invention.

Wires 46 connect lights 14 to light driver 34, illustrated in FIG. 4, so that lights 14 may be operated in sequence by light driver 34 as controlled by computer 28. Wires 46 connected to lights 14 pass through axial orifices 48 in light housing fixture 12.

Lights 14 are preferably equally circumferentially disposed about center line or axis 40, as depicted in FIG. 5, and are oriented with the center lines of lights 14, one of which is depicted schematically as 52 in FIG. 5 at an acute angle to the lower planar surface 38 of housing fixture 12, and hence, at an acute angle to surface 20 of test specimen 16 when surfaces 20 and 38 are in facing contact one with another. This acute angle is indicated as 50 in FIG. 5. Angle 50 is preferably about 45 degrees or less. Lights 14 are of the type which principally emit their radiation as a collimated beam generally along light center line 52 with relatively little scattering. Thus, radiation emitted by lights 14 travels generally as indicated by the portion of arrow 44 denoted as 44-1 before the light hits and is reflected by either the surface of indentation 18 or the portion of surface 20 surrounding indentation 18.

Due to the relatively low angle of incidence 50 between a beam for light 14 and surface 20, when a light as indicated by 14-1 is lit, the portion of indentation 18 closest to light 14-1 will be in shadow, as indicated by 18s in FIG. 5. The remainder of indentation 18 will appear to the radiation sensor to be more brightly lit, as will all of the portion of surface 20 of test specimen 16 surrounding indentation 18. The portion of surface 20 of test specimen 16 surrounding indentation 18 will appear to the radiation sensor to be of different brightness from the illuminated portion of indentation 18. Hence, several separate degrees of brightness or radiation intensity are sensed by the video camera 24, corresponding to the shadowed portion of indentation 18, the illuminated portion of indentation 18 and the illuminated portion of surface 20 surrounding indentation 18. Hence, a relatively high contrast exists at the edge of indentation 18 closest to light 14-1; this edge is indicated as 54 when light 14-1 is lit, and the other lights are not lit.

When light 14-3 is illuminated and light 14-1 is not energized, the situation reverses and the portion of indentation 18 closest to light 14-3 is in shadow, providing a high contrast at the portion of the edge of indentation 18 closest to light 14-3. Thus, by choosing which lights are lit at a given time, different portions of the edge of indentation 18 appear with high contrast respecting the remainder of impression 18 and surface 20 of test specimen 16 surrounding impression 18.

The configuration of light housing fixture 12, having generally longitudinally extending cylindrical wall portions 56 and generally radially inwardly extending top portion 58, shields Brinell impression 18 from noise light and noise radiation when housing fixture 12 is positioned over impression 18 as illustrated in FIG. 5. Central aperture 42 permits radiation reflected by impression 18 and the portion of surface 20 theresurrounding to escape upwardly, as indicated generally by arrow 44, for sensing by the video camera.

Figure 6:
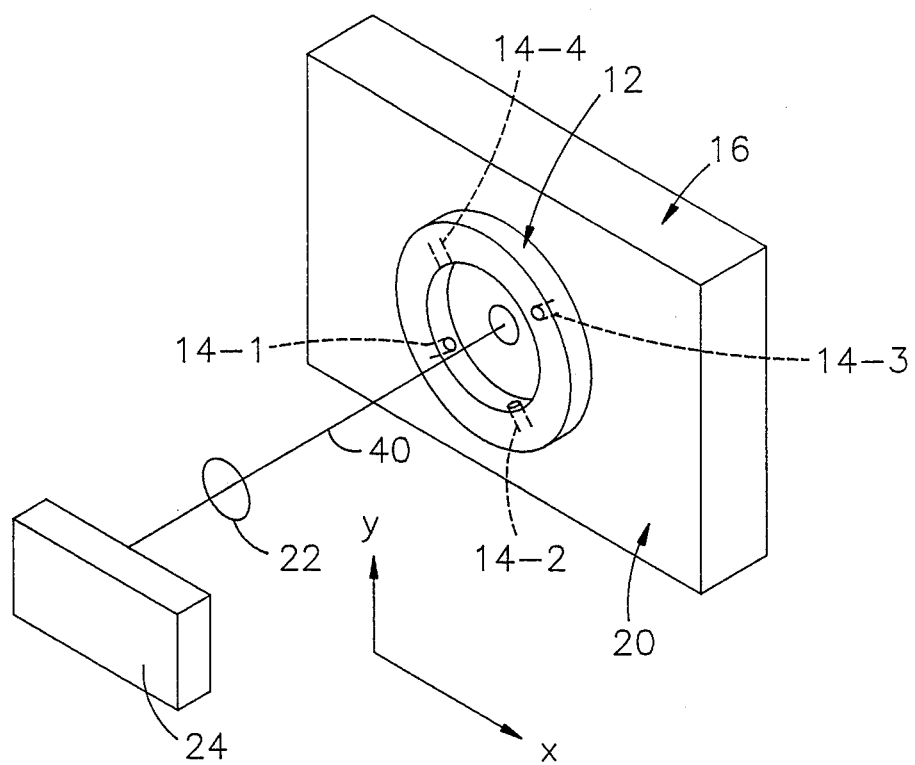
FIG. 6 is a schematic representation depicting geometric relationships of apparatus embodying aspects of the invention.

In FIG. 6, the test specimen has again been indicated generally as 16 with the test specimen surface in which Brinell impression 18 has been formed, again indicated as 20. Light housing fixture 12 is shown in foreshortened dimension with lights 14 illustrated as being equiangularly spaced about axis 40, which is an imaginary axis and does not represent any structure in the apparatus. Similarly, the radially inwardly extending top portion 58 of light housing fixture 12 has not been shown, to more illustrate the position of lights 14 within light housing fixture 12.

Referring to FIG. 7, computer 28 is connected to light driver 34 via line 60, which is grounded, and a line 62 which is one of four output data lines connecting computer 28 to light driver 34. Line 62, specifically all four of such lines 62, only one of which is illustrated in FIG. 7, connect the parallel interface connector of computer 28 to light driver 34; the parallel interface connector is denoted 64 in FIG. 7.

Light driver 34 includes an optocoupler designated generally 66, ground connections 68, 70, and an output line 82 running from light driver 34 to a selected light 14.

Optocoupler 66 includes a light emitting diode 74 and a light receiving phototransistor 76, operation of which is governed by light emitting diode 74. The emitter and collector junctions of phototransistor 76 are connected to ground, indicated by ground connection 68, and indirectly to a positive voltage source 78. Resistor 80 holds voltage at gate 90 of hexfet 88 positive when transistor 76 in optocoupler 60 is not conducting, thereby turning on hexfet 88.

Light driver 34 further includes an output line 82 connecting to light 14 and having a resistor 84 in series with an output terminal of hexfet 88. The voltage supplied via resistor 80 and controlled by transistor 76 is provided to a gate 90 of hexfet 88. The source terminal 92 of hexfet 88 is connected to ground via line 70 while the drain terminal 94 of hexfet 88 provides the output to light 14 through resistor 84 via line 82. Another resistor 86 reduces current provided via output data line 62 to a level suitable for input to light emitting diode 74.

Computer 28 controls lights 14 to operate in a selected sequence corresponding and in response to operation of software within the computer, which processes data resulting from the camera sensing electromagnetic radiation reflected by the Brinell indentation and the area of the specimen surrounded thereby. In response to a software command, a given light 14 or pair of adjacent lights is turned on when the corresponding data line(s) 64 is/are dropped to a low voltage. This causes current through resistor 86 and light emitting diode 74 of optocoupler 66 to drop nearly to zero thereby causing the light emitted by light emitting diode 74 to drop. This decline in output illumination turns transistor 76 of optocoupler 66 off, thereby effectively disconnecting the collector and emitter of transistor 76. Since the emitter of transistor 76 is now disconnected from ground, voltage at the gate of hexfet 88 rises due to the positive voltage applied from voltage source 78 through resistor 80. This positive voltage at gate 90 of hexfet 88 turns hexfet 88 on, allowing current to flow from positive voltage source 96 through hexfet 88 and resistor 83 thereby turning light 14 on by such current flowing through line 82.

Light driver 34 could also operate without resistors 86 and optocoupler 66 by connecting the gate of hexfet 88 directly to output data line 62 and changing the software in computer 28 to drive output data line 62 to a higher voltage, to turn light or lights 14 on.

The software in computer 28 is arranged to direct four active data lines simultaneously in order to turn lights 14 on in pairs so that two adjacent lights are on at a selected time to illuminate specified portions of the test specimen.

The video digitizer 26 is preferably a digital circuit board providing real time video digitization of the output received from the video camera resulting from the camera sensing radiation reflected by the Brinell indentation and the area of the specimen theresurrounding. One suitable video digitizer is the PCVisionPlus Frame Grabber available from Imaging Technology, Inc. for an IBM XT personal computer or equivalent clone.

During operation of the invention, the lights 14 are preferably operated in pairs, with each pair consisting of adjacent, rather than opposed, lights. Referring to FIG. 6, lights 14-1 and 14-2 are operated as one pair while lights 14-3 and 14-4 would be operated as the other pair. In FIG. 6, an arbitrary x-y coordinate system is indicated. When operating the invention to determine y coordinates of sensed images of interest, lights 14-1 and 14-2 would be operated as one pair of lights while lights 14-3 and 14-4 would be operated as the other pair of lights. When the pair of lights defined by lights 14-1 and 14-2 is illuminated, and the pair of lights defined by lights 14-3 and 14-4 is deenergized, the portion of indentation 18 closer to the lower portion of FIG. 6 will be in shadow while the portion of indentation 18 closer to the upper portion of FIG. 6 will be illuminated. Hence, accurate determination of the Y coordinate of the portion of the edge of indentation 18 closest to the bottom of FIG. 6 can be determined. When the pair of lights defined by 14-1 and 14-2 is deenergized and the pair of lights defined by lights 14-3 and 14-4 is energized, the edge of indentation closest to the top of FIG. 6 will be shadowed and an accurate determination of the y coordinate of that portion of the edge of indentation 18 can be made.

When determining the x coordinate of portions of the edge of indentation 18, lights 14-1 and 14-4 are operated as one pair of lights, and lights 14-2 and 14-3 are operated as the other pair of lights. When the pair of lights defined by lights 14-1 and 14-4 is energized, and the pair of lights defined by lights 14-2 and 14-3 is deenergized, the left-hand portion of indentation 18 in FIG. 6 will be shadowed while the right-hand portion of indentation 18 in FIG. 6 will be illuminated. Hence, accurate determination of the x coordinate of the left-hand edge of depression 18 can be made. Similarly, when the light pair defined by lights 14-2 and 14-3 is illuminated, and the light pair defined by lights 14-1 and 14-4 is deenergized, the right-hand portion of depression 18 in FIG. 6 will be shadowed, thereby permitting accurate determination of the x coordinate of that edge of indentation 18 by sensing the relative intensity of illumination reflected by that portion of indentation 18, the remainder of indentation 18 and the portion of surface 20 surrounding indentation 18.

One principal reason for illuminating the indentation along the x and y axes is that the Brinell test is classically performed by measuring two diameters of the Brinell impression, taken at 90 degrees to one another. By operating the lights as pairs, it is possible to obtain two diameters of the Brinell impression using the video digitizer and the video camera thereby providing a most accurate Brinell hardness reading for the test specimen of interest.

The video camera gathers radiation reflected by the workpiece including the Brinell indentation 18 in the workpiece area 20 surrounding indentation 18 and provides a signal indicative of the radiation reflected from indentation 18 and workpiece area 20 surrounding the indentation. The camera, as a video detector, detects relative radiation reflected by the indentation 18 in the area surrounding indentation 18 and provides an analog signal indicative of relative illumination detected, as reflected by the indentation and the workpiece area, for input to the video digitizer 26. The digitizer 26 converts the analog signal into a two-dimensional array of digital pixel signals corresponding to relative illumination reflected by the indentation and the two-dimensional area of the workpiece surrounding the indentation.

The computer, via appropriate software, detects an edge of the indentation by sensing the difference in electromagnetic radiation reflected by the indentation and the surrounding area and maps the sensed radiation to define a curve representing at least a portion of the edge of the indentation. The software within the computer computes diameter of the indentation for which the curve defines at least a portion of the indentation edge. Once indentation diameter is computed, the Brinell hardness for the test specimen is computed. Finally, the computed Brinell hardness is displayed by computer 28 on video monitor 32.

One of the steps of the method of the invention is to illuminate or irradiate the Brinell impression from opposite sides and to sense the reflected radiation when the indentation is irradiated from the two opposite sides. These sensed values of radiation, corresponding to the irradiation being applied from the respective sides, are algebraically substracted after the sensed values of reflected radiation have been converted to digital pixel intensities, to yield differential digital pixel intensities. This emphasizes the shadowed portions of the indentation and causes the reflected radiation received from the surface surrounding the indentation to effectively cancel itself out upon the algebraic subtraction of the radiation sensed when the test specimen is illuminated from two opposite sides, thereby providing an enhanced image of the indentation edge, for measurement purposes. The subtraction technique effectively eliminates optical noise signals which might otherwise be caused by spurious images appearing on the surface of the test specimen surrounding the indentation. Because the subtraction operation is performed algebraically, rather than arithmetically, the contrast between the shadowed and illuminated portions of the depression is further enhanced and magnified while the spurious optical signals received from extraneous images on the test specimen surrounding the indentation are effectively eliminated or minimized.

Because the sensed reflected radiations as produced by illuminating the depression from two different sides are the inverse of one another, by subtracting one set of reflected radiation signals from the other set of reflected radiation signals, the net result is to effectively add these signals together.

Figures 8, 9:
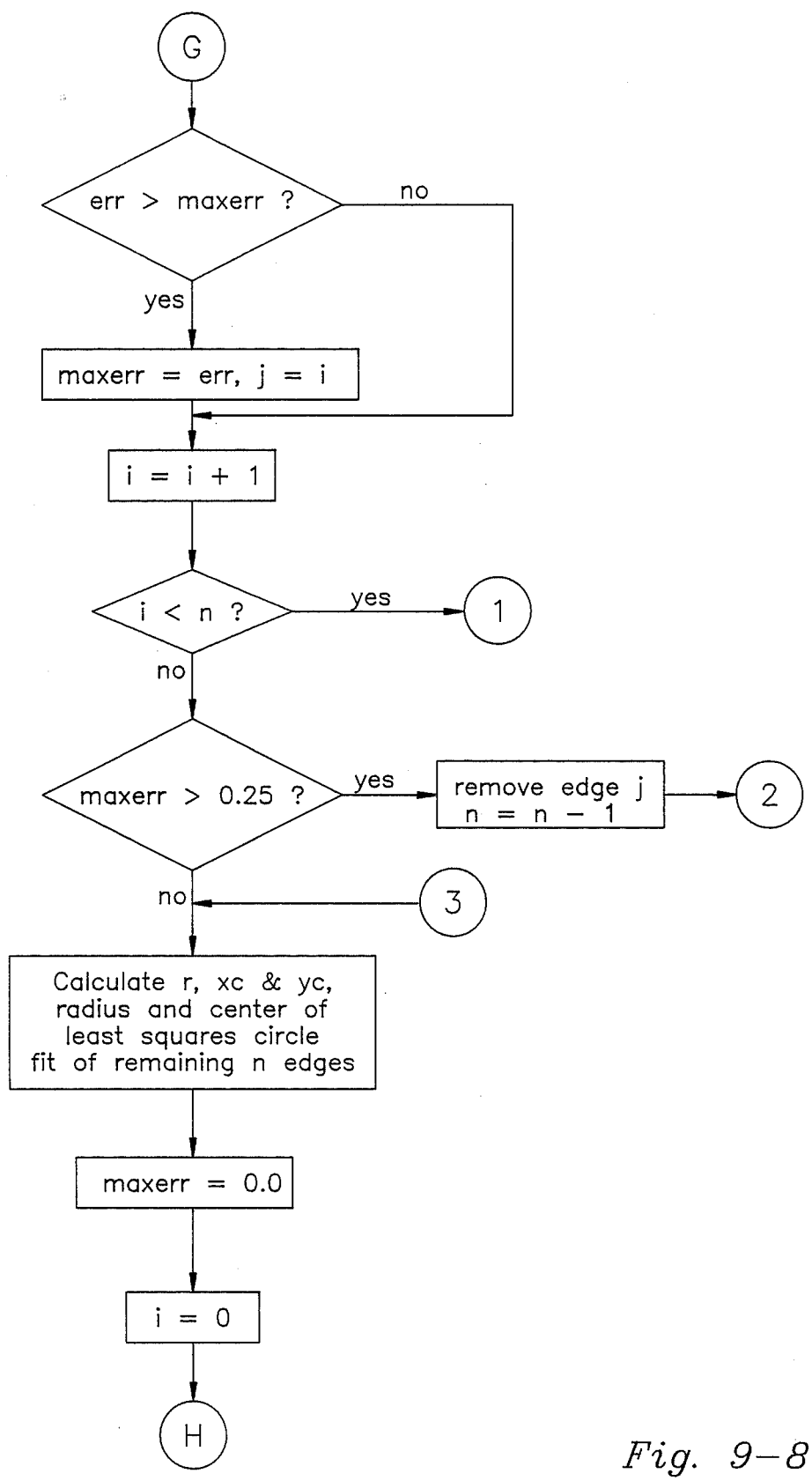
FIG. 8, consisting of FIGS. 8-A through 8-C, is a schematic diagram illustrating the camera or sensor pixel grid and its relationship to the light sources.
Figure 9:
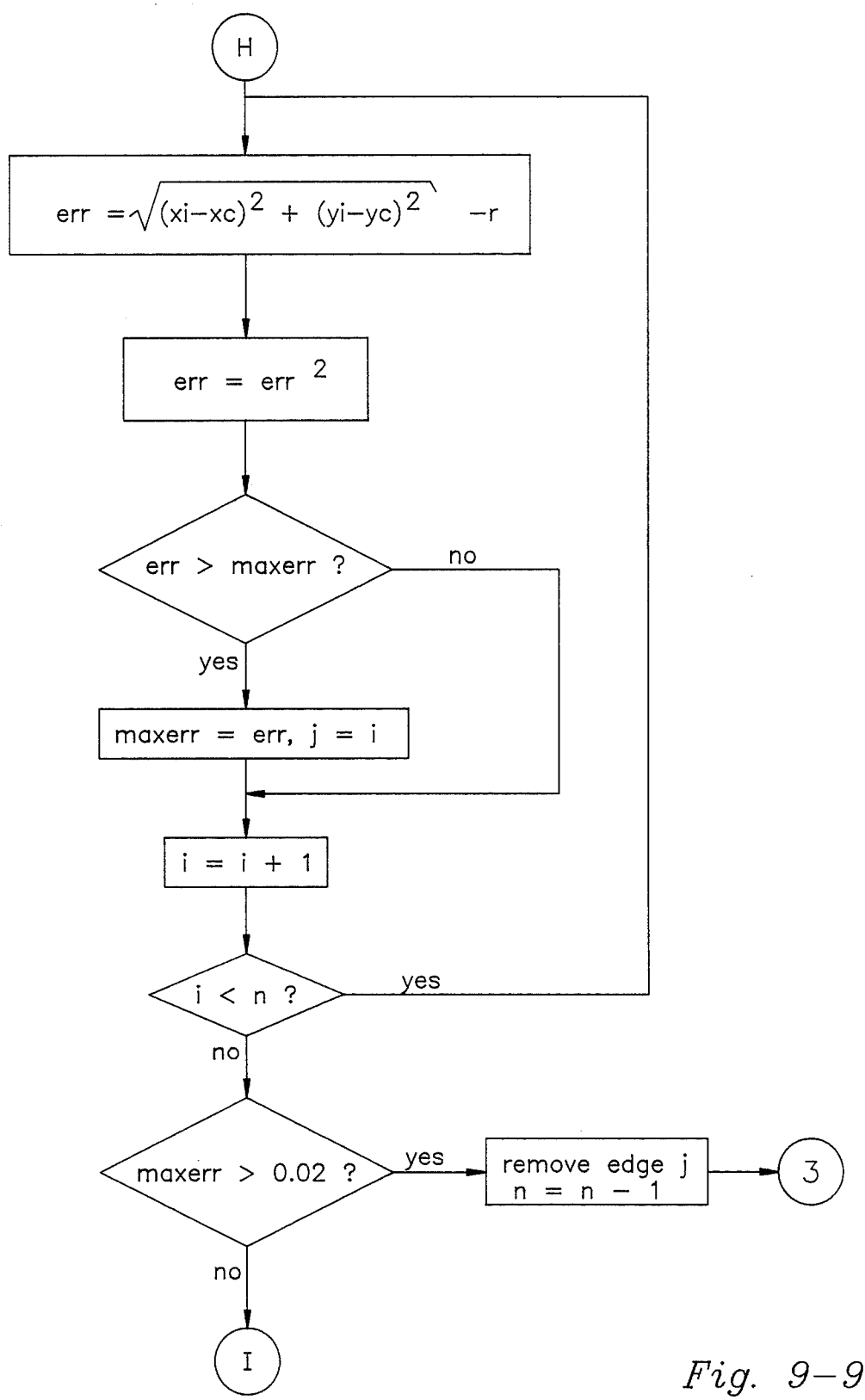
Figures 9, 10:
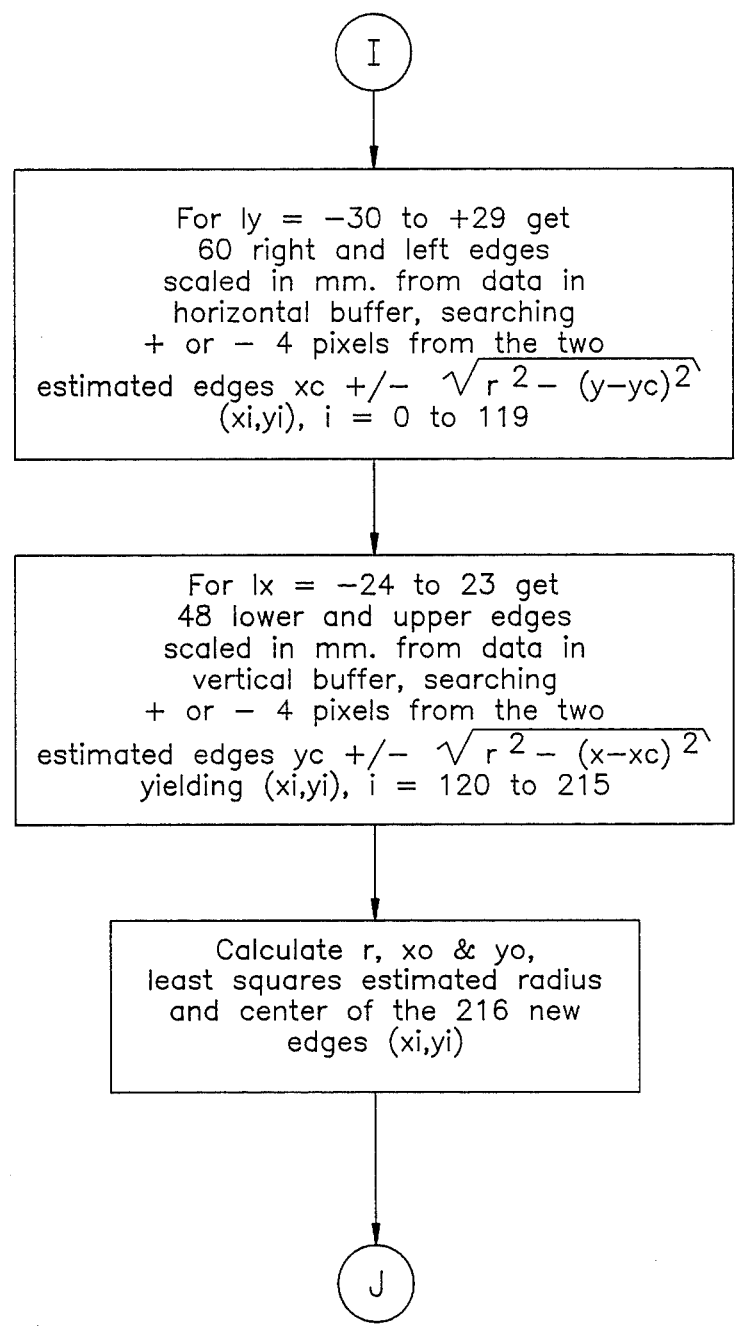
FIG. 10, consisting of FIGS. 10-1 through 10-3, is a schematic representation showing the variation in intensity of reflected radiation with distance across the test specimen, when the test specimen is irradiated from two different sides, and showing the results of algebraically substracting the values of reflected radiation one from another.
Figures 9, 10, 11:
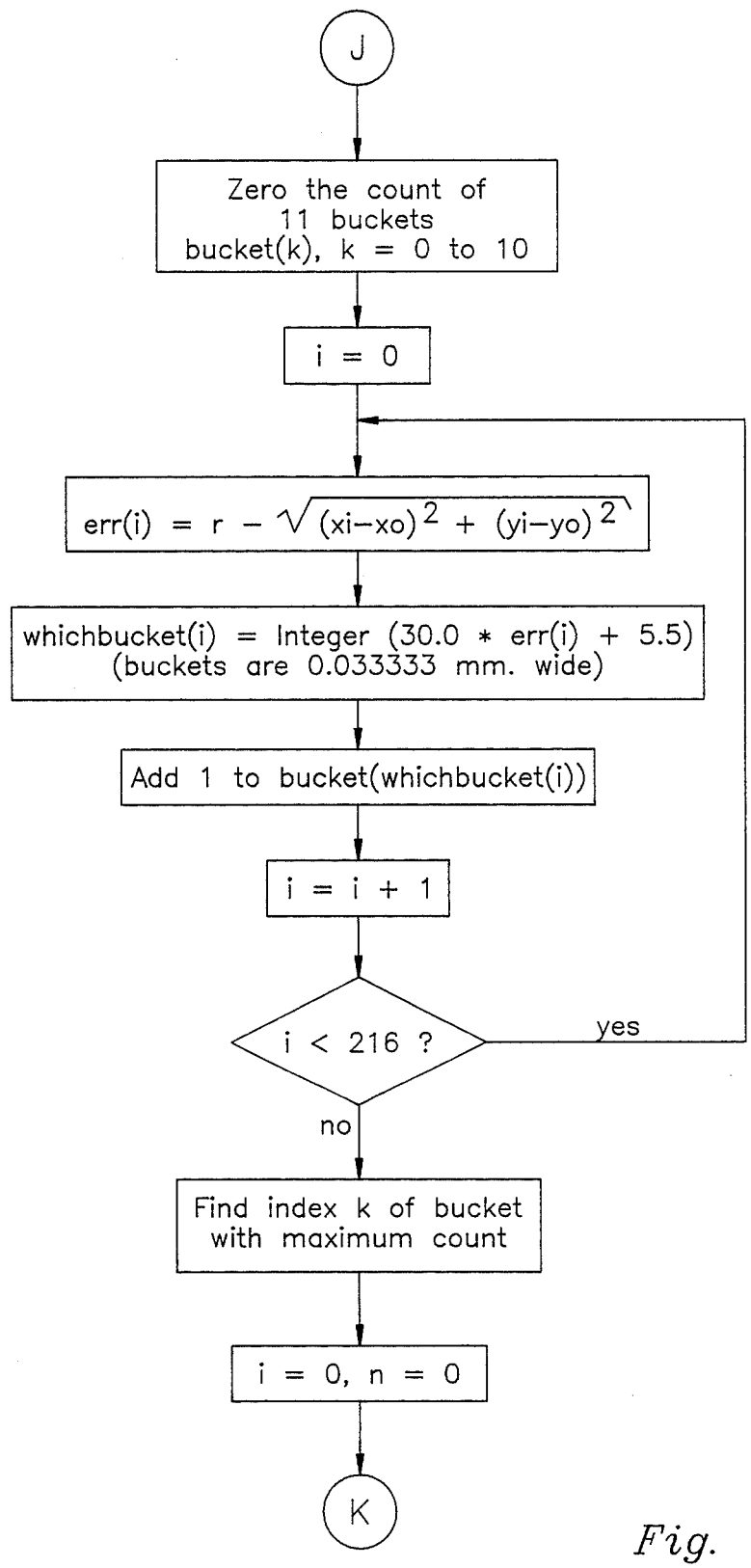
Figures 9, 10, 11, 12:
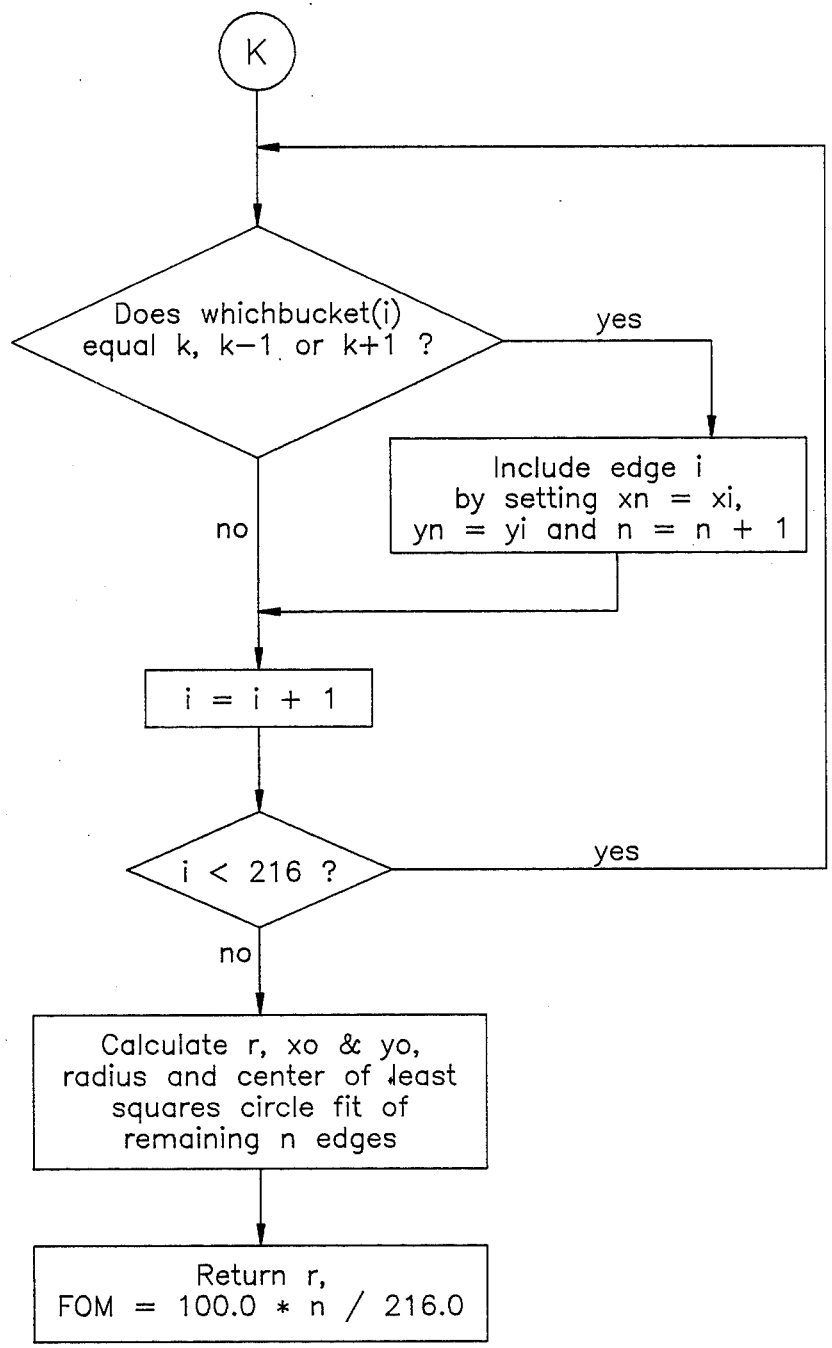
Figures 1, 10:
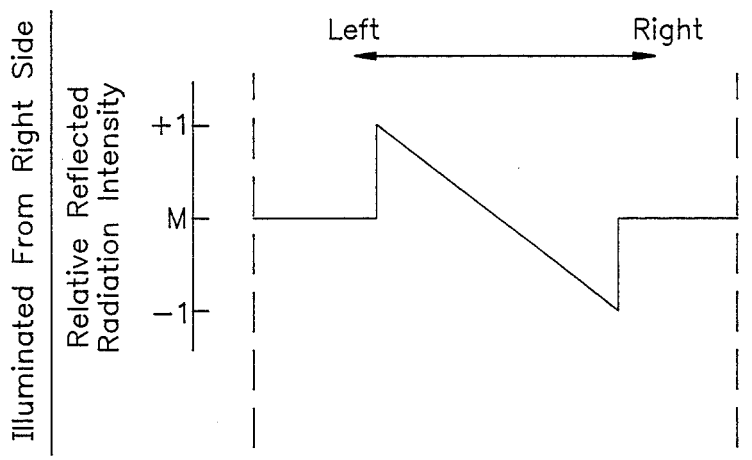
Figures 2, 10:
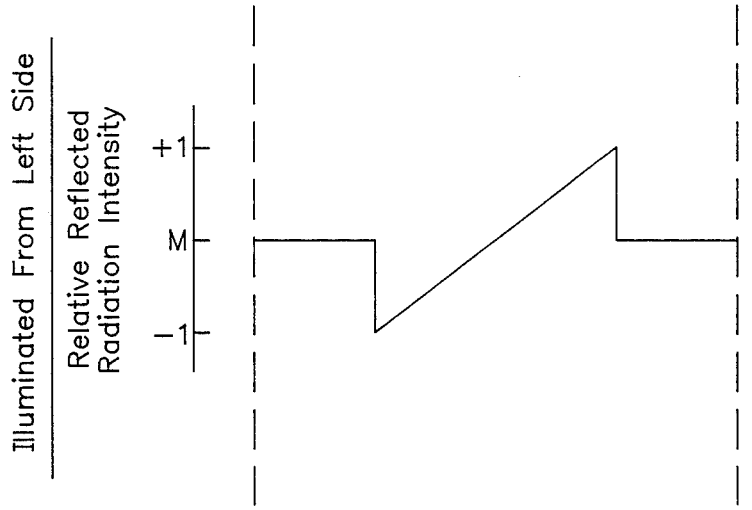
Figures 3, 10:
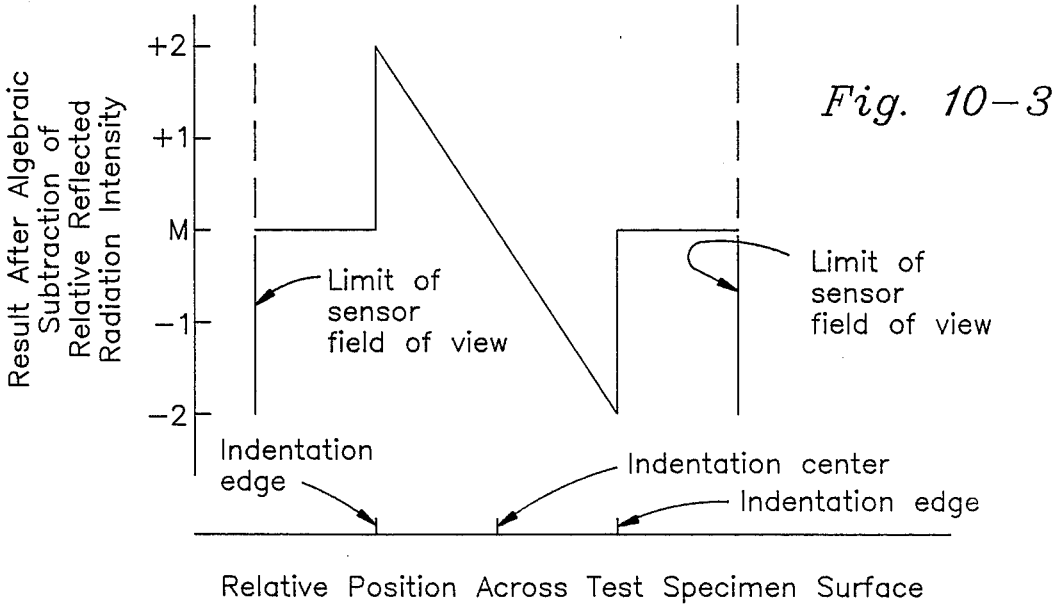

The results of this algebraic subtraction are illustrated in FIG. 10 where the top plot, FIG. 10-1, indicates sensed intensity of reflected radiation across the test specimen when illuminated from the right side, the middle plot, FIG. 10-2, indicates sensed intensity of reflected radiation across the test specimen when illuminated from the left side and the bottom plot, FIG. 10-3, illustrates the result of algebraically subtracting FIG. 10-2 from FIG. 10-1.

The apparatus may be combined with a device for applying a Brinell penetrator with preselected force according to Brinell test criteria to the specimen. In such case, the test specimen 16 is positioned respecting lens 22 and video camera 24 so that indentation 18 in specimen 16 is wholly within the field of view of video camera 24, and indentation 18 intersects the center of the field of view of the video camera. Once this has been accomplished, an initial estimate of the position of the center of the indentation, within the field of view of the electromagnetic radiation sensor defined by the camera and relative to an arbitrary x-y coordinate system established within that field of view, preferably having origin of the coordinate system coincident with the center of the camera field of vision, is obtained.

The following description of operation of the invention, particularly the software aspect of the invention, could be read in conjunction with the flowchart provided as FIGS. 9-1 through 9-12.

Electromagnetic radiation is applied via lamps 14 to indentation 18 and surface 20 theresurrounding from a first side of the field of view of video camera 24. For example, in FIG. 6, to determine x coordinate of points of interest, lights 14-2 and 14-3 might be illuminated simultaneously, as a first pair of lights. Camera 24 then senses radiation reflected by indentation 18 and the irradiated area of surface 20 immediately surrounding indentation 18 to determine first values of radiation reflected by indentation 18 and the immediately surrounding portion of area 20. These first values of reflected radiation are supplied as an analog signal from the camera to video digitizer 26 where they are converted into first digital pixel intensity signals, by video digitizer 26.

A portion of the first pixel intensity signals are read from the digitizer memory and stored as a first two-dimensional array of pixel intensities corresponding to a portion of the two-dimensional field of view of the sensor. (For determining the initial estimate of the position of the center of the indentation, only a portion of the first digital pixel intensity signals are used, in order to reduce computational time.) Typically, to determine the first estimate of location of the center of the indentation, ten rows in the x direction, and eight columns in the y direction, of digital pixel intensity signals within the first two dimensional array of digital pixel intensity signals may be used, where the ten rows and eight columns are contiguous with respective rows and columns and are located on either side of the center of the field of view of the camera. When processing the digital pixel intensity signals to determine locations of the center and edges of the indentation, the digital pixel intensity signals are preferably processed first on a row by row basis, to determine x coordinates of points of interest and then on a column by column basis, to determine y coordinates of points of interest. While this is not required, it is the way in which the invention is most efficiently practiced.

Next, electromagnetic radiation is applied to the indentation 18 and the area of surface 20 theresurrounding from a direction generally opposite that from which radiation was applied in the immediately preceding application. For example, upon the second application of radiation, lamps 14-1 and 14-4 in FIG. 6 might be used. The radiation reflected by indentation 16 and the irradiated area of surface 20 immediately surrounding indentation 18 is sensed as the radiation passes through lens 22 and reaches video camera 24 to determine second values of radiation reflected by indentation 18 and the immediately surrounding portion of surface 20. This determines second values of radiation reflected by indentation 18 and the immediately surrounding area, which is the radiation sensed when lamps 14-1 and 14-4 are illuminated and lamps 14-2 and 14-3 are off. These second values of reflected radiation are converted into second digital pixel intensity signals to define a second array of pixel intensities. The corresponding portion of the second array of pixel intensities is then subtracted from the stored portion of the first array of digital pixel intensities to obtain an array of differential digital pixel intensities. This array of differential digital pixel intensities is then stored for computational purposes.

Referring to FIG. 8, the top portion of FIG. 8, identified as FIG. 8-1 is a schematic representation of the sensor field of view showing the x, y coordinate system referred to in the software description and indicating the number of pixels in the sensor imaging system. The digitized image has 480 pixels vertically and 512 pixels horizontally. The origin of the coordinate system is arbitrarily selected so that the origin of the coordinate system is at the lower left-hand corner of a pixel, indicated as "origin" in FIG. 8-C, so that 240 rows of pixels are below the origin of the coordinate system and 240 rows of pixels, numbered beginning with the zeroth row through the 239th row, are above the origin. Likewise, 256 columns of pixels are to the left of the origin and 256 columns of pixels, numbered zero through 255, are to the right of the origin.

As indicated generally in FIG. 8-C, each pixel is 0.0325 mm wide and 0.026 mm high. The dimensions indicated in FIG. 8-A, namely 16.6 mm×12.4 mm, correspond to the field of view on the test specimen as viewed by the sensor through the lens. The lens effectively reduces this in half, down to the actual size of the radiation sensing surface in the camera. The pixel dimensions indicated in FIG. 8-C represent dimensions of the test specimen surface when divided into pixel equivalents. Consequently, when stored in the computer memory as provided by the video digitizer, the data for each pixel represents the data for a rectangular area measuring 0.0325 mm×0.026 mm on the test specimen surface. This dimension can vary slightly with various lenses.

FIG. 8-B is a schematic representation of the lights 14-1 through 14-4 and has depicted thereon the x, y coordinate system corresponding to the x, y coordinate system indicated in FIG. 8-A. Lights 14-1 and 14-4 operate as a pair, as do lights 14-2 and 14-3, when determining edge x coordinates. Similarly, lights 14-1 and 14-2 operate as a pair, as do lights 14-3 and 14-4, when determining edge y coordinates.

To determine an estimate of the x-coordinate of the center of the indentation relative to a preselected origin corresponding to the center of the field of view of the camera, rows of the stored array of differential digital pixel intensities are selected. From the selected rows, pixels having minimum and maximum intensities are selected. The x-coordinates of these selected pixels are averaged to obtain an estimate of the x-coordinate of the center of the indentation, which x coordinate is designated $C_x$. This procedure is illustrated in FIG. 9-1.

Once the estimate for the x coordinate of the indentation center has been obtained, an estimate of the y coordinate of the indentation center is similarly obtained. Specifically, electromagnetic radiation is applied to the indentation and the surrounding area from a first side of the field of view. For example, considering FIG. 6, the radiation might be applied by lights 14-1 and 14-2 being energized simultaneously with lights 14-3 and 14-4 deenergized. The radiation reflected by the indentation and the irradiated area immediately theresurrounding is sensed by camera 24 to determine third values (where "third" is used to distinguish these values from the "first" values sensed above in connection with determining an estimate of the x coordinate of the center of the indentation). The third values of reflected radiation are converted into third digital pixel intensity signals by digitizer 26. A portion of these third digital pixel intensity signals are read from the digitizer memory and stored as a two-dimensional array of pixel intensities corresponding to a portion of the two-dimensional field of view of the sensor or camera.

Electromagnetic radiation is then applied again to indentation 18 and the area theresurrounding from a direction generally opposite that from which the radiation was applied in obtaining the third values of radiation reflected by the indentation. Considering FIG. 6, lights 14-3 and 14-4 are illuminated and lights 14-1 and 14-2 are deenergized. Radiation reflected by the indentation 18 and the irradiated area immediately theresurrounding is sensed by video camera 24 to determine fourth values of radiation reflected by the indentation 18 and the immediately surrounding area. Video digitizer 26 converts the fourth values of reflected radiation into fourth digital pixel intensity signals. The computer then substracts the fourth array of digital pixel intensity signals from the third array of digital pixel intensity signals to obtain a second array of differential digital pixel intensities, which the computer stores.

An estimate of the y coordinate of the center of the indentation relative to a preselected origin corresponding to the center of the field of view of the video camera is determined by selecting from columns, of the stored array of differential digital pixel intensities, those pixels having minimum and maximum intensities and then averaging the y coordinates of those selected pixels to obtain an estimate of the y coordinate of the center of the indentation, which y coordinate is designated $C_y$. This procedure is illustrated in FIG. 9-2.

Once approximate x and y coordinates, designated $C_x$ and $C_y$, for the center of the impression have been determined, larger first and second arrays of differential digital pixel intensities are created by again sequencing the lights. A sixty (60) row by two hundred eighty-eight (288) pixel first array and a forty-eight (48) column by three hundred sixty (360) pixel array are created, centered at $C_x$ and $C_y$. This procedure is illustrated in FIGS. 9-3 and 9-4.

Data are generated to compute the initial estimate of the diameter of the impression. This is performed by computing an initial estimate of the location of the edges of the indentation.

The search is performed using an evenly spaced subset of rows and columns of these larger first and second arrays of differential digital pixel intensities. Eight rows of differential pixel intensities in the first array of differential pixel intensities and six columns of differential pixel intensities in the second array of differential pixel intensities are used to compute initial estimates of the location of the edge of the indentation.

The edge detection procedure is performed by computing the first derivative of pixel intensity at a particular pixel with respect to direction in a given array. For example, to compute an estimate of the x coordinate of the edge of the indentation along any particular row of differential pixel intensities, the first derivative of differential pixel intensity with respect to x is computed for each pixel of interest. This weighted derivative is computed using the formula:

$$\frac{dI_x}{d_x} = 4(I_{x+1} - I_x) + 3(I_{x+2} - I_{x-1}) + 2(I_{x+3} - I_{x-2}) + (I_{x+4} - I_{x-3})$$

where $I_x$ is the differential digital pixel intensity at a particular pixel located at position x in a row of pixels of interest, and the subscripts denote x locations in the row of differential digital pixel intensities of interest relative to the x location at which the weighted derivative of pixel intensity is being computed. The edge is considered located at the pixel where the derivative of differential digital pixel intensity, for a given row (or column) of pixels is a maximum.

Because eight rows of pixels are used to compute initial estimates of the location of the edge of the indentation, this yields 16 x coordinates, two in each of the eight rows, representing the x coordinates of the indentation edge. Similarly, because six columns of differential digital pixel intensities are used to compute location of the indentation edge when computing top and bottom locations of the edge in each of the six columns, 12 y coordinates, two for each of the eight columns of the digital differential pixel intensities, result. Hence, computation of the initial estimate of the location of the edges yields 28 sets of (x, y) points. This procedure is illustrated schematically in FIGS. 9-5 and 9-6.

The next step in the computational scheme is to screen the 28 sets of (x, y) points by calculating the radius to each of the 28 points from the first estimate of the center and then finding the average of that computed radius. All points more than one-half of a millimeter (0.5 mm) radius different from the previously computed average radius are then eliminated. These points are referred to as "one-half millimeter error points." Next, the average radius is recomputed after elimination of the one-half millimeter error points. This procedure of eliminating one-half millimeter error points and re-computing the average radius of circle after elimination of such one-half millimeter error points is repeated until all remaining points used in the computation of the average radius have an error of less than one-half millimeter (0.5 mm) difference from the computed average radius. This procedure is referred to as the first screen on radius. This procedure is illustrated in FIGS. 9-7 and 9-8.

The next step in the computational procedure is to perform a second screen on radius. In performing this step, the points remaining from the first screen on radius are used to make a new least square's estimate of the radius of the indentation and the coordinates of the center of the indentation, to obtain a third estimate of the coordinates of the center of the indentation and a second estimate of the radius of the indentation. The radius from the third center to every remaining point is computed and compared to the previously computed second estimate of radius which was computed as a portion of the first screen. Next, all points which are more than fifteen one-hundredths of a millimeter (0.15 mm) different from the second estimate of radius are eliminated. The least square—s estimate of the center and radius of the circle are then computed. This procedure is repeated with elimination of the 0.15 millimeter error points, by repeatedly computing the least square's estimate of the center and radius of the circle and repeatedly eliminating the 0.15 millimeter error points until no such points remain. Using this procedure, a third estimate of the position of the sensor of the indentation and a second estimate of the radius of the indentation is developed. This procedure is illustrated in FIGS. 9-8 and 9-9.

The next step in the computational scheme is to utilize the edge detector noted above to estimate a new edge position for the edge of the indentation within each of the 60 rows of digital pixel intensities and each of the 48 columns of digital pixel intensities which are the respective arrays of rows and columns of differential pixel intensities originally digitized from the analog data provided by the camera. The most recently estimated coordinates for the center of the indentation and the radius of the indentation are used to identify the narrow band of search for the edge detector within plus or minus four (4) pixels of the last estimated circle. By using the edge detector on these eight pixels, on four pixels on either side of the coordinate of the last estimated circle, 216 points result. Using these 216 points, 216 corresponding errors, which are the difference between the radius from the center of the circle to each estimated edge position minus the previously estimated least square's estimated radius, are computed. The 216 errors are then partitioned into eleven equal ranges. The highest population range is selected together with immediately adjacent ranges on either side of the highest population range. All other estimated edges, falling in ranges other than the three selected, are discarded. The final least square's estimate of the radius of the circle is computed using the edge locations within the selected highest population range and the two immediately adjacent ranges. Finally, a figure of merit defined by the percent of edge locations used in computing the final least square's estimate of the radius of the indentation based on the 216 available points for computation is computed. Finally, once the radius of the indentation is computed, a Brinell hardness is computed and displayed using a conventional Brinell hardness computation technique. This procedure is illustrated in FIGS. 9-10, 9-11 and 9-12.

What is claimed is:

1. An apparatus for determining Brinell hardness of a metal specimen which has been indented by a Brinell penetrator applied with a preselected force according to Brinell test criteria, comprising:
   a. means for applying electromagnetic radiation to said indentation and an area of the specimen surrounding the indentation at an acute angle relative to an axis perpendicular to a surface of said specimen surrounding the indentation whereby a portion of said electromagnetic radiation is reflected by said indentation and by said surrounding area:
   b. means for detecting and mapping intensities of said reflected radiation for at least a portion of said indentation and at least a portion of said area theresurrounding;
   c. means for determining derivatives of mapped intensity of reflected radiation with respect to a change in position on said map for at least two points located on said map;
   d. means for computing a location of a curve representing an edge of said indentation using said derivatives;
   e. means for computing a diameter of said indentation using said location of the curve;
   f. means for computing Brinell hardness of said specimen from said computed diameter;
   g. means for displaying said computed Brinell hardness.

2. Apparatus of claim 1 wherein said electromagnetic radiation is visible light.

3. Apparatus of claim 1 wherein said radiation applying means further comprises means for applying a beam of radiation to said indentation and said specimen area theresurrounding.

4. Apparatus of claim 3 wherein said means for applying a beam of radiation further comprises means for applying a plurality of beams of radiation to said indentation and said specimen area theresurrounding at a plurality of locations spaced angularly about said indentation.

5. Apparatus of claim 4 wherein said plurality of angular locations are symmetrically spaced about said indentation.

6. Apparatus of claim 5 wherein said beams of radiation are all applied to said indentation and said test specimen at a common angle of incidence.

7. Apparatus of claim 6 further comprising means for sequentially applying said plurality of beams to said indentation and specimen area theresurrounding.

8. Apparatus of claim 5 wherein said plurality is four.

9. Apparatus of claim 8 wherein said plurality of beams of radiation are applied to said specimen simultaneously.

10. Apparatus of claim 1 wherein said electromagnetic radiation is infrared.

11. Apparatus of claim 1 wherein said detecting means further comprises means for viewing said specimen including said indentation and the specimen area theresurrounding, detecting reflected radiation of the viewed area and providing a signal indicative of reflected radiation being detected at positions viewed over said indentation and said specimen theresurrounding.

12. Apparatus of claim 11 wherein said means for viewing said specimen further comprises means for detecting relative intensity of the reflected radiation at discrete positions in the viewed area and providing a signal indicative of relative intensity detected at positions over said indentation and said specimen area theresurrounding.

13. Apparatus of claim 1 wherein said curve is closed.

14. A method for determining Brinell hardness of a metal specimen which has been indented by a Brinell penetrator applied with a preselected force according to Brinell test criteria, comprising:
   a. applying electromagnetic radiation to said indentation and an area of the specimen surrounding the indentation at an acute angle relative to an axis perpendicular to a surface of said specimen surrounding the indentation thereby a portion of said electromagnetic radiation is reflected by said indentation and by said surrounding area;
   b. detecting and mapping intensities of said reflected radiation for at least a portion of said indentation and at least a portion of said area theresurrounding;
   c. determining derivatives of a mapped intensity of said reflected radiation with respect to a change in position on said map for at least two points located on said map;
   d. computing a location of a curve representing an edge of said indentation using said derivatives;
   e. computing a diameter of said indentation using said location of the curve;
   f. computing Brinell hardness of said specimen from said computed diameter;
   g. displaying said computed Brinell hardness.

15. The method of claim 14 wherein said detecting further comprises:
   a. viewing said specimen including said indentation and the area theresurrounding;
   b. detecting reflective radiation of the viewed area; and
   c. providing a signal indicative of reflected radiation detected at positions viewed over said indentation and said area theresurrounding.

16. The method of claim 15 wherein said electromagnetic radiation is visible light.

17. The method of claim 15 wherein said electromagnetic radiation is infrared.

18. An apparatus for determining Brinell hardness of a metal specimen, comprising:
   a. means for contacting said specimen with a Brinell penetrator and applying a predetermined load to said specimen through said penetrator according to standardized Brinell test criteria so as to produce an indentation in said specimen;
   b. means for applying electromagnetic radiation to said indentation and an area of the specimen surrounding the indentation at an acute angle relative to an axis perpendicular to a surface of said specimen surrounding the indentation whereby a portion of said electromagnetic radiation is reflected by said indentation and by said surrounding area;

c. means for detecting and mapping intensities of said reflected radiation for at least a portion of said indentation and at least a portion of said area theresurrounding;

d. means for determining derivatives of mapped intensity of said reflected radiation with respect to a change in position on said map for at least two points located on said map;

e. means for computing a location of a curve representing an edge of said indentation using said derivatives;

f. means for computing a diameter of said indentation using said location of the curve;

g. means for computing Brinell hardness of said specimen from said computed diameter;

h. means for displaying said computed Brinell hardness.

19. Apparatus of claim 18 wherein said electromagnetic radiation is visible light.

20. Apparatus of claim 18 wherein said electromagnetic radiation is infrared.

21. Apparatus of claim 18 wherein: i. said radiation applying means further comprises means for applying a plurality of beams of radiation to said indentation and said specimen area theresurrounding at a plurality of locations spaced angularly about said indentation; ii. said plurality of angular locations are symmetrically spaced about said indentation; and iii. said beams of radiation are all applied to said indentation and said test specimen at a common angle of incidence.

22. A method for determining Brinell hardness of a metal test specimen having been indented with a Brinell penetrator applied with preselected force according to Brinell test criteria, comprising the steps of:

a. applying electromagnetic radiation to said indentation and an area theresurrounding from a first side;

b. sensing radiation reflected by said indentation and the irradiated area immediately theresurrounding to determine first reflected radiation pixel intensities corresponding to the indented area of the specimen and area theresurrounding;

c. applying electromagnetic radiation to said indentation and the area theresurrounding in a side different from said first side;

d. sensing radiation reflected by said indentation and an irradiated area immediately theresurrounding to determine second reflected radiation pixel intensities corresponding to the indented area and the area theresurrounding;

e. combining said first and second pixel intensities to obtain differential pixel intensities;

f. computing diameter of said indentation from said differential pixel intensities; and g. computing Brinell hardness from said indentation diameter.

* * * * *